(12) United States Patent
Bai et al.

(10) Patent No.: US 12,194,311 B2
(45) Date of Patent: Jan. 14, 2025

(54) METHOD FOR CONSTRUCTING PHOTON SOURCE MODEL FUNCTION OF MEDICAL LINEAR ACCELERATOR

(71) Applicant: Harbin Medical University, Harbin (CN)

(72) Inventors: Yanling Bai, Harbin (CN); Zhenguo Cui, Harbin (CN); Yewei Wang, Harbin (CN); Qi Liu, Harbin (CN); Lina Feng, Harbin (CN)

(73) Assignee: Harbin Medical University

( * ) Notice: Subject to any disclaimer, the term of this patent is extended or adjusted under 35 U.S.C. 154(b) by 353 days.

(21) Appl. No.: 17/828,070

(22) Filed: May 31, 2022

(65) Prior Publication Data

US 2022/0401754 A1    Dec. 22, 2022

(30) Foreign Application Priority Data

Jun. 10, 2021   (CN) .......................... 202110645477.5

(51) Int. Cl.
*A61N 5/10*   (2006.01)
*G21G 1/12*   (2006.01)
*H05H 9/04*   (2006.01)

(52) U.S. Cl.
CPC ................. *A61N 5/10* (2013.01); *H05H 9/04* (2013.01); *G21G 1/12* (2013.01)

(58) Field of Classification Search
CPC ........ G16H 20/40; G16H 40/63; G16H 50/50; A61N 5/103; A61N 5/1031; A61N 2005/1041; A61N 2005/1055; A61N 2005/1089; A61N 2005/1035; A61N 5/10; A61N 2005/1034; A61N 5/1048; A61N 5/1045; A61N 5/1042; A61N 2005/1087; A61N 5/1064; A61N 5/1001; A61N 2005/1091; A61N 2005/1095; G06N 3/09; G06N 3/084; G06N 3/0442; G06N 3/0475; G06N 7/01; G06N 3/0464; G06N 20/00; H05H 9/04; G21G 1/12; G21K 5/04; G21K 5/10; G21K 1/04; G21K 1/046;

(Continued)

(56) References Cited

U.S. PATENT DOCUMENTS

| 5,625,663 A * | 4/1997 | Swerdloff ............... G21K 1/046 378/65 |
| 6,029,079 A * | 2/2000 | Cox ..................... A61N 5/1031 600/407 |
| 2011/0293071 A1 * | 12/2011 | Torsti ................... A61N 5/1048 378/152 |

* cited by examiner

*Primary Examiner* — Irakli Kiknadze
(74) *Attorney, Agent, or Firm* — Hawaii Patent Services; Nathaniel K. Fedde; Kenton N. Fedde

(57) ABSTRACT

A method for constructing a photon source model function of a medical linear accelerator, for calculating the dose of rays in a radiation therapy scheme is disclosed. A source model of a therapeutic photon beam of the accelerator includes a primary ray photon source model and a scattered ray photon source model. Physical parameters in the two parts of source model functions include the position coordinates of an emission point of a particle, a projection value of a unit momentum vector in a three-dimensional orthogonal direction, and the energy of the particle. By utilizing the model functions, photon fluence information, energy spectrum information, and unit momentum direction information of photons on any phase space plane can be accurately calculated. The method and thought for constructing the source model are applicable to construction of source models of photon beams with various nominal energies of the accelerator used in a radiation therapy.

6 Claims, 13 Drawing Sheets

(58) Field of Classification Search
CPC ..... G21K 1/093; G06F 30/25; G06F 2111/08; G01T 1/02
USPC .......................................................... 378/65
See application file for complete search history.

METHOD FOR CONSTRUCTING PHOTON SOURCE MODEL FUNCTION OF MEDICAL LINEAR ACCELERATOR

FIELD

The disclosure relates to the technical field of radiation dose measurement, and in particular, to a method for constructing a photon source model function of a medical linear accelerator.

BACKGROUND

Radiation therapy is a method that depends on high-energy ionizing rays to treat tumors, and constitutes three mainstream means for treating tumors together with a surgical treatment method and a medical treatment method. During radiation therapy, the killing probability of tumor cells and the degree of damage to normal tissues are related to the level of radiation doses. Therefore, when an irradiation scheme is designed, the radiation therapy needs to concentrate the ray dose from different directions to irradiate on the tumor to disperse the dose of the normal tissues, so that the dose in the tumor area can be increased to a great extent, the dose of normal tissues and organs can be reduced, and the irradiation volume of the normal tissues can be minimized as much as possible. Therefore, at the stage of designing the radiation therapy scheme, the accuracy of dose calculation is very important.

The radiation therapy has a history of nearly a hundred years, and there are various dose calculation methods or calculation models for the radiation therapy, which are continuously advanced and developed. Nowadays, the most widely used clinical dose calculations are mathematical analysis methods, such as a pencil beam algorithm, an AAA algorithm, an XB algorithm, and an iterative convolution algorithm. However, when theses algorithms are in non-uniform tissue, especially in an area with a large density difference, the calculation error is relatively large, which can reach in a range of 4% to 17%.

The Monte Carlo dose calculation method is currently recognized as the most accurate and precise calculation method, and is based on a mathematical method of sampling in statistical physics. Through the mathematical methods of statistical physics, atomic physics and nuclear physics theories, a transport process of particles in a medium can be accurately simulated, and various information about the transport process of the particles can be recorded. The Monte Carlo dose calculation process can be divided into two stages according to a physical stage, including: (1) simulating and tracking the electrons bombarding a target, calculating and tracking an interaction between the electrons and target atoms, bremsstrahlung photons generated during interaction, and a process that the bremsstrahlung photons are trimmed by a flattening filter, and recording photon particle information of the trimmed therapeutic ray beam; and (2) tracking the transport process of photons of the therapeutic ray beam in the body of a patient, and recording information in the transport process. In the actual treatment scenario, the patient to be treated can be changed in rotation, but the photon source device of the medical linear accelerator is unchanged. Therefore, in a pretreatment stage, a plane (generally, the plane is selected to be under a ray beam flattening filter of the accelerator) vertical to the ray beam is selected at an appropriate position in an internal space of a head of the accelerator. Information of the photons of the therapeutic ray beam reaching the plane is recorded. The photon information includes the position coordinates, movement momentum directions and energy of the photons on the plane. The recorded photon information is stored in a file. The file is also known as a phase space file. The plane is also known as a phase space plane. When patient dose calculation is needed, the phase space file is used as a phase space plane source input file of particles to be directly used for dose calculation. Therefore, a simulation process in the head of the accelerator at the first stage can be omitted, massive calculation time can be saved, and working efficiency can be enhanced.

However, since the phase space file must record enough particles (billions) to ensure that the variance of the particle fluence in the phase space plane is small enough, resulting in overlarge file size to occupy very large hard-disk space. In addition, during dose calculation, the importing of particle information into a computing program from a hard disk is very time-consuming. An inherent statistical variance of the particle fluence on the phase space plane may be further transmitted to the follow-up dose calculation process. In addition, once the phase space file is formed, the number and distribution size of the recorded particles cannot be changed, and cannot vary with the irradiation field as well. Therefore, currently, it is the best choice to replace the phase space with a mathematical function description method. Through parameters in a mathematical function, physical characteristics of a particle source, including the particle energy characteristics emitted by the source, the spatial position of a particle emission point, and the distribution characteristics of the particle momentum direction, are accurately expressed. The mathematical function is directly used as a description function of a Monte Carlo dose calculation particle input source, so that the phase space file is no longer needed. Therefore, time is saved, convenient calculation is achieved, and the calculation efficiency and variance can be significantly improved.

In the prior art, a method for establishing a source model function for photon dose calculation of a medical linear accelerator used for Monte Carlo dose calculation includes: establishing a spatial geometry-based projection relationship using photons at a target position and fall point positions of photons in the phase space, then establishing a mathematical form of photon physical parameters, and establishing the source model function by introducing a concept of a photon ring.

During the establishment of the source model function, the photons from a tungsten target position are known as primary ray photons. These primary ray photons have different emission directions (that is, a momentum direction). After the primary ray photons are grouped according to the momentum direction, the primary ray photons may form ring-band distribution on any phase space plane, which is the so-called photon ring. Therefore, after the photons on the phase space plane acquired through Monte Carlo calculation are grouped according to the momentum direction, a ring-by-ring highlight distribution area may occur. The photons in the highlight annular area are the primary ray photons, and the rest of the photons are scattered ray photons. There is no focus area, as shown in FIG. 1.

As shown in FIG. 2, a high-energy electron beam vertically bombards a thin tungsten target after being led out, so that X-ray photons are generated. The number of the photons at any effective point is directly proportional to the intensity (number) of the electron beam bombarding the point. An established mathematical model is as follows:

$$p_{pp,i}(u,v|r,E) = \int (u-u_0)(v-v_0)\frac{-b \pm \sqrt{b^2-4ac}}{2a} e^{-\frac{x_s^2+y_s^2}{2\delta_s^2}} dx_s dy_s$$

$$u_0 = \frac{r-x_s}{\sqrt{(r-x_s)^2+y_s^2+z_{phsp}^2}}$$

$$v_0 = \frac{-y_s}{\sqrt{(r-x_s)^2+y_s^2+z_{phsp}^2}}$$

$(x_s, y_s)$ represents position coordinates of the photons on the target plane, r represents a distance from fall points of the photons on the phase space plane from a center, (u, v, w) are three component projections of the photons in a direction of unit momentum, $\delta_s$ is a distribution variance of the electron beam bombarding the target. $\delta(u-u_0)$ or $\delta(v-v_0)$ is an impulse function, $(u_0, v_0)$ is a component of the photons falling onto a plane of a radiation field in the direction of momentum, and $z_{phsp}$ a distance from the phase space plane (the plane of the radiation field) from a source.

A scattered photon source model function: since the direction of momentum of the scattered photons is chaotic, but the momentum component of the photons meets $u^2+v^2+w^2=1$, which is a spherical surface, the distribution of the scattered photons on the spherical surface after the scattered photons are grouped according to the momentum distribution is shown in FIG. 3. Fitting of directions (u and v) is performed according to its probability distribution characteristics, the distribution probability of the scattered photons corresponding to different w is a Gaussian function, so that a plurality of Gaussian functions of the scattered photons on the spherical surface can be obtained by fitting. Based on fitted results and angles of the scattered photons, in a radius area of the phase space plane, the momentum distribution of the scattered photons is:

$$p_{ps,j}(\alpha,\beta,r,E) = \sum_{k=1}^{K} G_{i,k}(\alpha,\beta) = \sum_{k=1}^{K} \frac{c_{i,k}}{2\pi \times \sigma_{\alpha,i,k} \times \sigma_{\beta,i,k}} \cdot e^{-\frac{(\alpha-\mu_{i,k})^2}{2\sigma_{\alpha,i,k}^2} - \frac{\beta^2}{2\sigma_{\beta,i,k}^2}}$$

wherein $\alpha$ and $\beta$ are respectively direction angles corresponding to projections u and v in the direction of momentum.

However, the above model function has at least the following disadvantages:

(1) Number distribution information of the photons on an active plane is $$\frac{1}{2\pi\sigma_s^2} e^{-\frac{x_s^2+y_s^2}{2\sigma_s^2}}.$$

After the photons emitted by the target are filtered by the flattening filter, the distribution function of photon fluence is already different from the photon fluence emitted by the target. Therefore, the distribution of photon fluence cannot be described by a single Gaussian function.

(2) Information of the photons in the direction of momentum is provided in the form of photon distribution radius. The photons uniformly distributed on a ring band have a same projection w in the direction of momentum. However, due to the presence of the indispensable flattening filter inside the head of the accelerator, fluence distribution of bremsstrahlung photons on the target plane and fluence distribution of the primary ray photons after being affected by the flattening filter have different forms.

(3) Emission directions of the photons can be determined or fall point positions on the plane can be calculated, but the fluence probability of the primary ray photons in the direction, or the photon fluence probability in the momentum direction of the photons, cannot be provided. Therefore, the above model function cannot be used for a source model in Monte Carlo dose calculation.

(4) A primary ray photon distribution function after being affected by the flattening filter is not a simple two-dimensional Gaussian function. In this model, if the fluence distribution function of the photons on a source plane is expressed as photon distribution generated by the target of the accelerator, it lacks of the action of the flattening filter. If it is expressed in the form of the distribution of the primary ray photons after being affected by the flattening filter, the function is not a simple Gaussian function, because particle fluence distribution after the bremsstrahlung photons generated by the target pass through the flattening filter is no longer in a bell shape, fluence distribution information of the photons cannot be truthfully reflected. Therefore, the function is not applicable to calculation of the dose of complex radiation fields or delicate fields.

(5) The description of the model function for the function of the scattered photons is very complex. It is tedious for the function to calculate the positions and component information in the direction of momentum of the scattered photons.

(6) The above model function lacks weight information of particle distribution on different ring bands.

SUMMARY

Therefore, in view of the technical problems in the prior art, the disclosure provides a new method for constructing a photon source model function of a medical linear accelerator. The method is used for calculating the dose of rays in a radiation therapy scheme, has advantages of being less in modeling parameters, clear in physical significance of parameters in the function and convenient to use, and can faithfully reproduce photon fluence distribution information, and unit momentum direction information and energy information of photons in a radiation field at any position and height.

Specifically, the method is mainly implemented by means of the following technical solutions.

A method for constructing a photon source model function of a medical linear accelerator is disclosed. A photon source model of the medical linear accelerator includes a primary ray photon source model and a scattered ray photon source model. The method includes:

turning on the medical linear accelerator, bombarding an X-ray target of the medical linear accelerator using a generated high-energy electron beam, storing information, recorded on an initial phase space plane, of bremsstrahlung photons generated on a target plane in a first phase space file, and storing photon information, recorded on a phase space plane, of a therapeutic photon beam passing through a flattening filter in a second phase space file;

converting the first phase space file and the second phase space file into phase space files which are respectively denoted as B-PhSp and R-PhSp on the target plane through photon reverse flight calculation, and separating photons recorded in the phase space file R-PhSp into primary ray photons and scattered ray photons to obtain two new phase space files which are respectively denoted as p-PhSp and s-PhSp;

constructing a primary ray photon source model function according to the fluence distribution function of the bremsstrahlung photon, a fluence probability distribution function of bremsstrahlung photons emitted from a fluence point on the target plane in a momentum component, and a fluence probability distribution function of the bremsstrahlung photons emitted from the fluence point on the target plane and absorbed by the flattening filter in a direction of the momentum component; and constructing a scattered ray photon source model function according to the fluence distribution function of the scattered ray photon and an average fluence probability distribution function of scattered photons emitted by all fluence points on a target plane in the momentum component.

Preferably, separating photons recorded in the phase space file R-PhSp into primary ray photons and scattered ray photons specifically includes: in the photons recorded in the phase space file R-PhSp, denoting photons of which position coordinates are located in a geometric projection area of a conical aperture of a primary collimator on a bottom end surface of the target as the primary ray photons, the primary ray photons being able to return to the initial phase space plane along the aperture of the primary collimator; and denoting photons outside the geometric projection area as the scattered ray photons.

Preferably, position coordinate parameters of the photons recorded in the phase space file B-PhSp and the phase space file p-PhSp are placed at a center point (0, 0, 0) of the target plane, wherein the target plane is set as a 0-reference plane, which is equivalent to the number of the bremsstrahlung photons generated at the center of the target plane when the number of electrons bombarding the target is increased several times, and the number of photons from the center point of the bottom end face of the target in a primary ray photon beam at this time.

Preferably, the photons expressed by the photon source model function of the accelerator are photons with energy of one spectral line in an energy spectrum of a photon beam. Therefore, the bremsstrahlung photons of a continuous energy spectrum are divided into a plurality of energy groups which are represented by $E_i$ by using an energy width $Bin_E$, wherein i is a natural number, $E_i$ represents a median energy distribution of the ith group of photons, also known as the energy $E_i$ of the i th spectral line, and an energy distribution width of the group of photons is $(E_i \pm \frac{1}{2} \cdot Bin_E)$.

Preferably, the step of constructing a primary ray photon source model function specifically includes as follows:

The bremsstrahlung photon fluence distribution function is:

$$N_{B,E_i}(x_s, y_s) = \sum_i N_{B,E_i}(x_s, y_s) = P_{B,E_i} * N_B(x_s, y_s) = P_{B,E_i} \cdot N_{B0} * e^{-\frac{x_s^2 + y_s^2}{2\sigma^2}};$$

and $$N_{B,E_i} = \iint N_{B,E_i}(x_s, y_s) * dx_s dy_s = \iint P_{B,E_i} * N_B(x_s, y_s) * dx_s dy_s = P_{B,E_i} * N_B;$$

wherein $P_{B,E_i}$ is a branching ratio of $N_{B,E_i}(x_s, y_s)$ at $N_B(x_s, y_s)$, $N_{B,E_i}$ represents a total count of the bremsstrahlung photons of which energy is $E_i$, $N_B$ represents a total count of the bremsstrahlung photons with all energies, and $N_{B0}$ represents the count of the bremsstrahlung photons generated at the center point of the target;

the fluence distribution function of the bremsstrahlung photons in the direction of the momentum component obtained through fitting of the fluence distribution of the bremsstrahlung photons in the direction of the momentum component is:

$$N'_{B,E_i}(p_x, p_y) = a'_{E_i,1} * e^{-\frac{p_x^2 + p_y^2}{2\sigma_{B,E_i,m_1}^2}} + a'_{E_i,2} * e^{-\frac{p_x^2 + p_y^2}{2\sigma_{B,E_i,m_2}^2}};$$

wherein $N_{B,E_i}'(p_x,p_y)$ represents the fluence distribution of the bremsstrahlung photons in the ith energy group generated in the center point of the target in the direction of the momentum component; $\sigma_{B,E_i,m_1}$ and $\sigma_{B,E_i,m_2}$ are fluence distribution standard deviations of the photons of which energy is $E_i$ in the bremsstrahlung photons in the direction of the momentum component, $a'_{E_i,1}$ and $a'_{E_i,2}$ are coefficients of a function expression, which equal to the count of the bremsstrahlung photons emitted at an angle of 0 degree, a flight momentum direction of the bremsstrahlung photons is expressed by a projection value of a unit momentum on a three-dimensional rectangular coordinate system, that is, $(p_x, p_y, p_z)$, and $p_x^2 + p_y^2 + p_z^2 = 1$; and B represents the bremsstrahlung photons, $E_i$ represents the energy of the i th spectral line, m represents momentum, that is, $\sigma_{B,E_i,m_1}$ and $\sigma_{B,E_i,m_2}$ are two standard deviations of momentum distribution.

Since angular fluence probabilities of the bremsstrahlung photons generated by all fluence points on the target plane are the same, the fluence probability distribution function of the bremsstrahlung photons emitted from the fluence point on the target plane in the momentum component is:

$$P'_{B,E_i}(p_x, p_y) = \frac{N'_{B,E_i}(p_x,p_y)}{\iint N'_{B,E_i}(p_x,p_y) \cdot dp_x dp_y} = a_{E_i,1} * e^{-\frac{p_x^2 + p_y^2}{2\sigma_{B,E_i,m_1}^2}} + a_{E_i,2} * e^{-\frac{p_x^2 + p_y^2}{2\sigma_{B,E_i,m_2}^2}};$$

wherein $a_{E_i,1}$ and $a_{E_i,2}$ are coefficients of a fluence probability distribution function expression of the bremsstrahlung photons in the direction of the momentum component, which are obtained according to normalization calculation of $a'_{E_i,1}$ and $a'_{E_i,2}$.

The fluence distribution of the bremsstrahlung photons absorbed by the flattening filter in the direction of the momentum component is obtained according to a difference between the fluence distribution of the bremsstrahlung photons in the direction of the momentum component and fluence distribution of the primary ray photons in the direction of the momentum component, and the fluence distribution function of the bremsstrahlung photons absorbed by the flattening filter in the direction of momentum component is obtained through fitting, which is:

$$N'_{(f-absorbed),E_i}(p_x, p_y) =$$

$$b'_{E_i,1} * e^{-\frac{p_x^2+p_y^2}{2\sigma^2_{(f-absorbed),E_i,m_1}}} + b'_{E_i,2} * e^{-\frac{p_x^2+p_y^2}{2\sigma^2_{(f-absorbed),E_i,m_2}}};$$

wherein $N'_{(f-absorbed),E_i}(p_x,p_y)$ represents fluence distribution of the bremsstrahlung photons absorbed by the flattening filter and with the energy of the ith spectral line in the direction of momentum component $(p_x,p_y)$; $\sigma_{(f-absorbed),E_i,p_1}$ and $\sigma_{(f-absorbed),E_i,p_2}$ are respectively standard deviations of the above two two-dimensional Gaussian functions; and $b'_{E_i,1}$ and $b'_{E_i,2}$ are respectively coefficients of the above two Gaussian function expressions.

The total count of the bremsstrahlung photons with the energy of the ith spectral line at any fluence point is mathematically normalized to obtain the fluence probability distribution function of the bremsstrahlung photons emitted from the fluence point on the target plane and absorbed by the flattening filter in the direction of momentum component, which is:

$$P'_{(f-absorbed),E_i},(p_x, p_y)] = \frac{N'_{(f-absorbed),E_i}(p_x, p_y)}{\int\int_{-m}^{m} N'_{(f-absorbed),E_i}(p_x, p_y)dp_x dp_y} =$$

$$b_{E_i,1} * e^{-\frac{p_x^2+p_y^2}{2\sigma^2_{(f-absorbed),E_i,m_1}}} + b_{E_i,2} * e^{-\frac{p_x^2+p_y^2}{2\sigma^2_{(f-absorbed),E_i,m_2}}};$$

wherein $P'_{(f-absorbed),E_i}(p_x,p_y)$ is the probability of the bremsstrahlung photons absorbed by the flattening filter; and $b_{E_i,1}$ and $b_{E_i,2}$ are respectively two coefficients of a probability distribution model function, and obtained through mathematical normalization calculation of $b'_{E_i,1}$ and $b'_{E_i,2}$.

The fluence probability distribution function of the primary ray photons emitted by the fluence point on the target plane is obtained according to a difference between the fluence probability distribution function of the bremsstrahlung photons emitted from the fluence point on the target plane in the momentum component and the fluence probability distribution function of the bremsstrahlung photons emitted from the fluence point on the target plane and absorbed by the flattening filter in the direction of momentum component, and by combining the fluence distribution function of the bremsstrahlung photons, the primary ray photon source model function is obtained, which is:

$$N_{E_i}(x_s,y_s,p_x,p_y)=N_{B,E_i}(x_s,y_s)*[P'_{B,E_i}(p_x,p_y)-P'_{(f-absorbed),E_i}(p_x,p_y)];$$

wherein $$N_{B,E_i}(x_s, y_s) = N_{B,E_i,0} * e^{-\frac{x_s^2+y_s^2}{2\delta^2}} = P_{B,E_i} * N_{B0} * e^{-\frac{x_s^2+y_s^2}{2\delta^2}} = P_{B,E_i} * N_B(x_s, y_s);$$

and $$P'_{B,E_i}(p_x, p_y) =$$

$$\frac{N'_{B,E_i}(p_x, p_y)}{\int\int N'_{B,E_i}(p_x, p_y) \cdot dp_x dp_y} = a_{E_i,1} * e^{-\frac{p_x^2+p_y^2}{2\sigma^2_{B,E_i,m_1}}} + a_{E_i,2} * e^{-\frac{p_x^2+p_y^2}{2\sigma^2_{B,E_i,m_2}}};$$

and $$P'_{(f-absorbed),E_i},(p_x, p_y)] = \frac{N'_{(f-absorbed),E_i}(p_x, p_y)}{\int\int_{-m}^{m} N'_{(f-absorbed),E_i}(p_x, p_y)dp_x dp_y} =$$

$$b_{E_i,1} * e^{-\frac{p_x^2+p_y^2}{2\sigma^2_{(f-absorbed),E_i,m_1}}} + b_{E_i,2} * e^{-\frac{p_x^2+p_y^2}{2\sigma^2_{(f-absorbed),E_i,m_2}}};$$

wherein the primary ray photon source model is located on the 0-reference plane, the flight momentum direction of the primary ray photons is expressed by the projection value of the unit momentum on the three-dimensional rectangular coordinate system, that is, $(p_x,p_y,p_z)$, and $p_x^2+p_y^2+p_z^2=1$, therefore, $z_s$ and $p_z$ are omitted; each parameter in the above function expression is given in a process of fitting the function, and $P'_{B,E_i}(p_x,p_y)$ represents the fluence probability distribution of the bremsstrahlung photons in the momentum component; $P'_{(f-absorbed),E_i}(p_x,p_y)$ is the probability of the bremsstrahlung photons absorbed by the flattening filter; $a_{E_i}{}^1$ and $a_{E_i,2}$ are coefficients of the fluence probability distribution function of the bremsstrahlung photons in the momentum component, and $\sigma_{B,E_i,m1}$ and $\sigma_{B,E_i,m2}$ are the distribution standard deviations of the fluence probability distribution function of the bremsstrahlung photons in the momentum component; and $b_{E_i,1}$ and $b_{E_i,2}$ are coefficients of the fluence probability function of the bremsstrahlung photons in the momentum component, $\sigma_{(f-absorbed),E_i,m1}$ and $\sigma_{(f-absorbed),E_i,m1}$ are standard deviations of the probability function of the bremsstrahlung photons absorbed by the flattening filter, and (f-absorbed) is an identification indicating being absorbed by the flattening filter.

Preferably, the step of constructing a scattered ray photon source model function specifically includes:

discretizing a distribution area of the scattered photons recorded in the phase space file s-PhSp of the scattered photons to form a pixel grid, acquiring the fluence distribution of the scattered photons on the 0-reference plane in a unit of the pixel grid, and performing fitting on the fluence distribution of the scattered photons by using a double gaussian function polynomial to obtain a fluence distribution function of the scattered photons, which is:

$$N_{scatter,E_i}(x_s, y_s) = a_i * e^{-\frac{x_s^2+y_s^2}{2\sigma^2_{s,E_i,1}}} + b_i * e^{-\frac{x_s^2+y_s^2}{2\sigma^2_{s,E_i,2}}};$$

wherein $(x_s,y_s)$ is position coordinates of any point on the 0-reference plane, $N_{scatter,E_i}(x_s,y_s)$ represents the number of the scattered photons at the fluence point $(x_s,y_s)$, $a_i$ and $b_i$ are coefficients of a fitting function of the fluence distribution of the scattered photons of which energy is $E_i$; $\sigma_{s,E_i,1}$ and $\sigma_{s,E_i,2}$ are distribution standard deviations of the fitting function of the fluence distribution of the scattered photons of which energy is $E_i$; and s in a parameter subscript represents a scattered ray identification.

The fitting function of the fluence distribution of the scattered photons emitted by each fluence point on the plane on which the target is located in the momentum component is:

$$N_{scatter,E_i}(p_x, p_y) = \begin{cases} a'_i * e^{-\frac{p_x^2+p_y^2}{2\sigma_{s,E_i,m1}^2}} + b'_i * e^{-\frac{p_x^2+p_y^2}{2\sigma_{s,E_i,m2}^2}}; & \text{function variable domain: } p_x^2 + p_y^2 > r^2 \\ c'_i * (p_x^2 + p_y^2) + d'_i; & \text{function variable domain: } p_x^2 + p_y^2 \le r^2 \end{cases}$$

wherein parameters $a'_i$, $b'_i$, $c'_i$ and $d'_i$ are coefficients of the fitting function of the fluence distribution in the momentum component; and $\sigma_{sE_i,m1}^2$ and $\sigma_{s,E_i,m2}^2$ are standard deviations of the fitting function of the fluence distribution in the momentum component. In a subscript of each parameter, i represents an identification of an energy group of the ith spectral line; and then, an average fluence probability distribution function of the scattered photons in the momentum component is obtained according to the fluence distribution function of the scattered photons in the momentum component, which is:

$$P'_{scatter,E_i}(p_x, p_y) = \begin{cases} a_i * e^{-\frac{p_x^2+p_y^2}{2\sigma_{s,E_i,m1}^2}} + b_i * e^{-\frac{p_x^2+p_y^2}{2\sigma_{s,E_i,m2}^2}}; & \text{function variable domain: } p_x^2 + p_y^2 > r^2 \\ c_i * (p_x^2 + p_y^2) + d_i; & \text{function variable domain: } p_x^2 + p_y^2 \le r^2 \end{cases}$$

wherein a function domain r is given by using the following mathematical method:

$$a_i * e^{-\frac{r^2}{2\sigma_{s,E_i,m1}^2}} + b_i * e^{-\frac{r^2}{2\sigma_{s,E_i,m2}^2}} = c_i * r^2 + d_i$$

The parameters $a_i$, $b_i$, $c_i$, $d_i$, $\sigma_{sE_i,m1}^2$ and $\sigma_{s,E_i,m2}^2$ in the average fluence probability distribution function of the scattered photons in the momentum component are given by a fitting process, wherein $a_i$, $b_i$, $c_i$ and $d_i$ are coefficients of the function, $\sigma_{s,E_i,1}$ and $\sigma_{s,E_i,2}$ are distribution standard deviations distributed along the momentum, these parameters are closely related to energy, and are able to be fitted to the energy to respectively form a relationship function between each parameter and the energy.

The scattered photon source model function constructed according to the fluence distribution function of the scattered photons and the average fluence probability distribution function of the scattered photons emitted by all fluence points on the target plane in the momentum component is:

$N_{scatter,E_i}(x_s,y_s,z_s,p_x,p_y,p_z,E_i) = N_{scatter,E_i}(x_s, y_s, z_s) * P'_{scatter,E_i}(p_x,p_y,p_z)$.

Compared with the prior art, the disclosure has the following beneficial effects.

The model function disclosed in the disclosure is less in modeling parameters, clear in expressed physical significance and convenient to use. The model function directly and clearly includes complete characteristic value information of the photons in the therapeutic photon beam of the accelerator. The information includes position coordinates of the initial emission point of photons, the projection of the particles in the orthogonal coordinate system in the direction of the unit momentum, and the energy of the particles. By using the mathematical function, the space distribution function of the photon fluence and the angular distribution function of the photon fluence on the source plane are intuitively reflected. Through the utilization of the model function, the photon fluence information, energy spectrum information, and photon unit momentum direction information of the therapeutic photon beam of the accelerator on any phase space plane can be directly and accurately calculated. Therefore, the model function has the advantage of faithfully reproducing the photon distribution information of a radiation field by using a mathematical analysis method. Photon sample size of simulation calculation can be randomly set according to requirements. By adopting the model function to calculate the photon distribution on any phase space plane, there is no statistical fluctuation variance. In this way, variance and convergence of the dose calculation can be greatly improved. Bytes occupied by the storage of the model function are extremely small and can even be ignored, thus propagation and use of the model function are facilitated.

The method and thought for constructing the source model involved in the disclosure are applicable to the construction of source models of photon beams with various nominal energies of the accelerator used in a radiation therapy, and can be used for Monte Carlo dose calculation of the therapeutic photon beam of the accelerator and the development of related products.

DETAILED DESCRIPTION OF THE EMBODIMENTS

In order to enable those skilled in the art to understand the core idea of the disclosure more clearly, the disclosure will be described below in detail with reference to the accompanying drawings.

Figure 15:
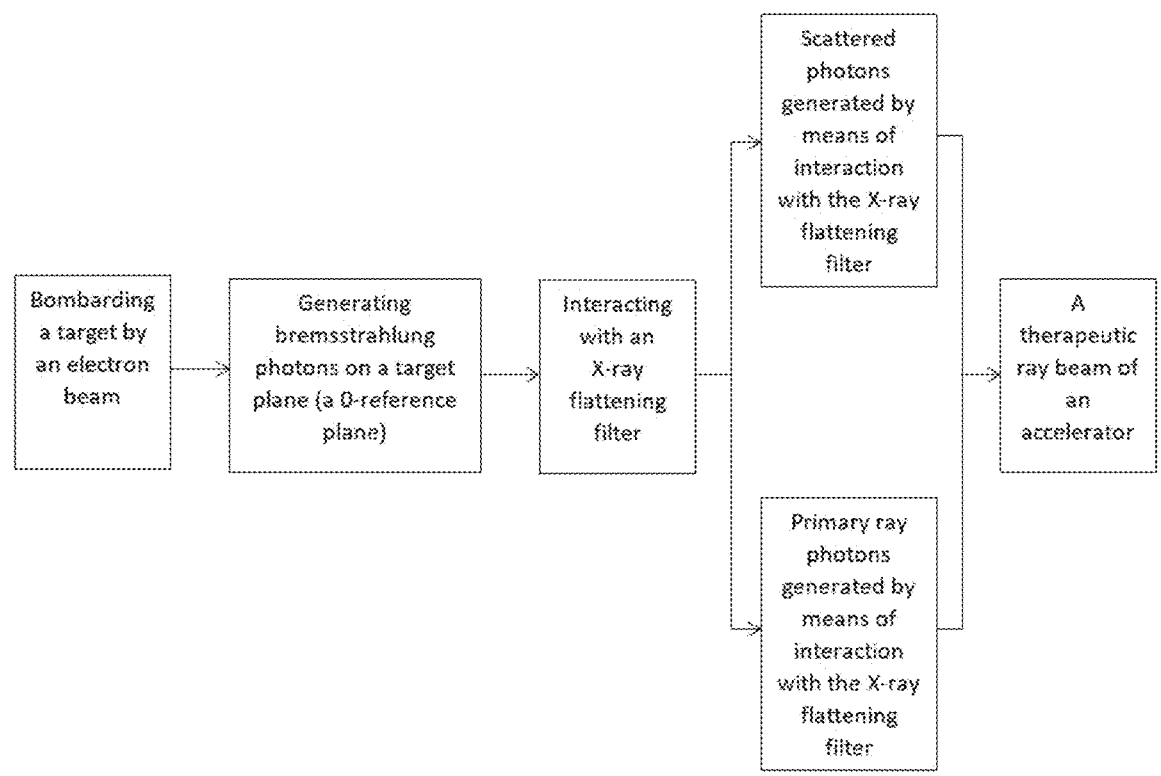
FIG. 15 is a physical flowchart of generating a therapeutic photon beam by a medical linear accelerator according to an embodiment of the disclosure.

The method for constructing a photon source model function of a medical linear accelerator provided by the disclosure is mainly used for calculating the dose of rays in a radiation therapy scheme and for particle source calculation of a Monte Carlo method. An involved medical linear accelerator includes an X-ray target, a ray source device, an accelerating tube, a flattening filter and a collimator system. The collimator system includes a primary collimator system and a secondary collimator system. The physical flowchart of generating a therapeutic photon beam by a medical linear accelerator is shown as FIG. 15: hot electrons emitted after heating by an electron gun filament of the ray source device are focused into an electron beam with a diameter of 1-2 mm, the electron beam is led into the accelerating tube and accelerated by a microwave electric field, and is led out after being accelerated to a predetermined energy height, the high-energy electron beam led out of an exit window bombards an X-ray tungsten target (being regarded as a thin target according to the thickness, the thickness being less than 1 mm, which may be 0.89 mm), to generate a large quantity of bremsstrahlung photons on a target plane, and the bremsstrahlung photon beam becomes a therapeutic photon beam after passing through a tapered hole of the primary collimator and the flattening filter. The tungsten target is inlaid in a copper target substrate. A cooling system of the copper target substrate will take away the large amount of heat generated in a process that the electron beam bombards the target. It should be noted that, the therapeutic photon beam of the above accelerator contains a large quantity of photons from the target. This part of photons is known as primary ray photons. The photon beam further contains a large quantity of scattered photons generated due to the fact that initial movement direction and energy of this part of initial bremsstrahlung photons are changed in a process of passing through the flattening filter caused by a photoelectric effect, a compton effect, a pair effect and a rayleigh scattering effect generated by that bremsstrahlung photons continuously interact with the flattening filter during the interaction with the target substrate and the ray beam flattening filter. The primary ray photons may spatially form focus spots on the target plane, that is, a target plane of the accelerator. The scattered photons have no focus spots.

The construction of a photon source model function of a medical linear accelerator in the disclosure adopts a double-source model manner. The photon source model includes a primary ray photon source model and a scattered photon source model. However, parameters of the two parts of source model functions are state information of the photons, that is, position coordinates $(x_s, y_s, z_s)$ of the photons, a projection $(p_x, p_y, p_z)$ of a unit momentum in an orthogonal coordinate system and energy E. The position coordinates of the photons adopt a rectangular coordinate system. A momentum direction of the photons is described by a projection value of the unit momentum of the photons in the rectangular coordinate system, that is, a momentum component, represented as $p_x$, $p_y$, $p_z$, and $p_x^2+p_y^2+p_z^2=1$. There is a clear and understandable proportional relationship between the primary ray photon source model and the scattered photon source model. Since the huge quantity of bremsstrahlung photons generated by the tungsten target of the accelerator are distributed within a continuous energy spectrum, and can be discretized into a series of spectral lines. The energy of each spectral line is expressed with $E_i$, and there are a large quantity of photons in each spectral line.

Figure 16:
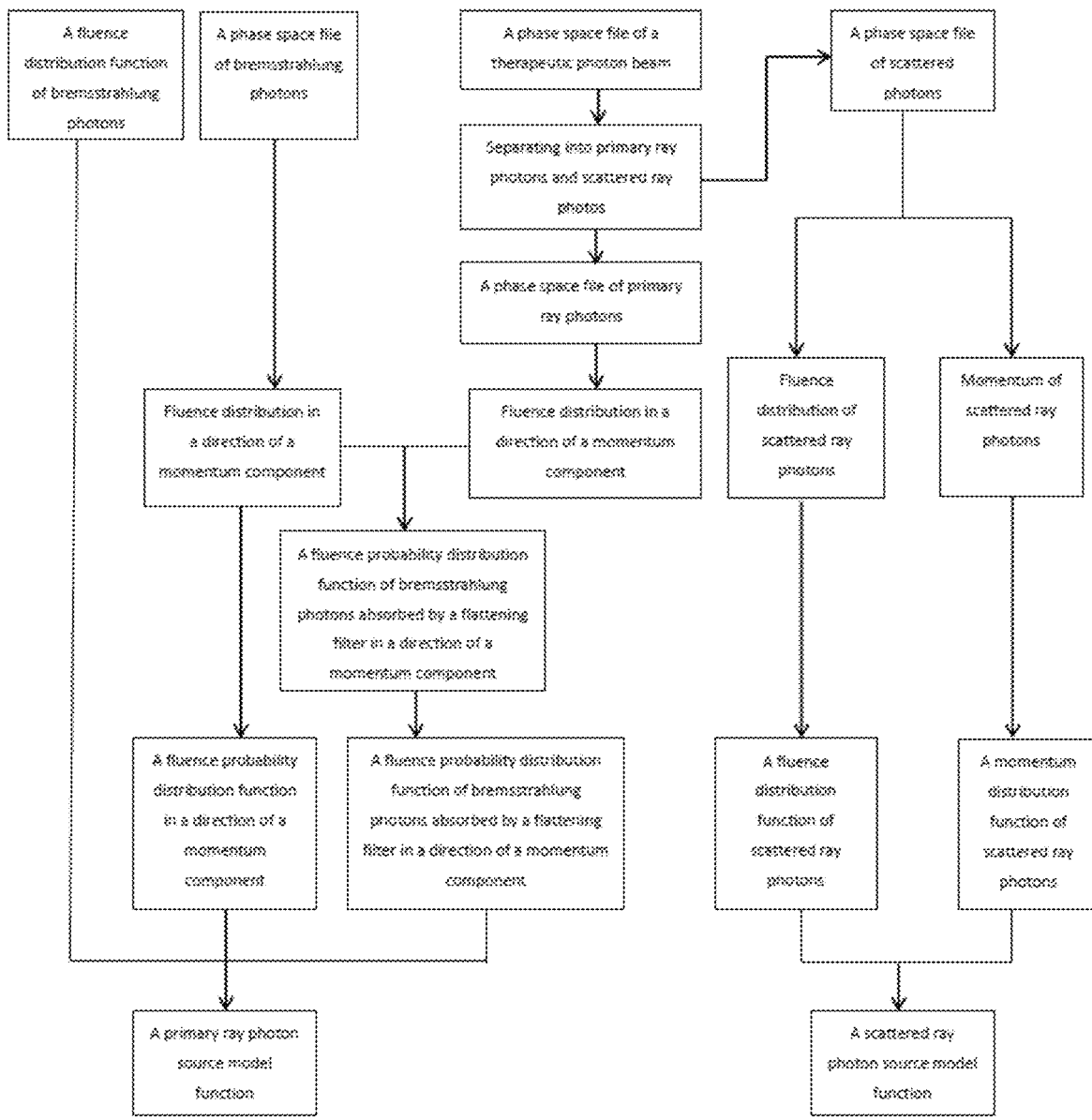
FIG. 16 is a flowchart of a method for constructing a photon source model function of a medical linear accelerator according to an embodiment of the disclosure.

FIG. 16 is a schematic flowchart of a method for constructing a photon source model function of a medical linear accelerator according to the disclosure. The method for constructing the photon source model function of the medical linear accelerator is described in detail in conjunction with FIG. 4 to 14. By taking the medical linear accelerator having a 4 MV photon beam as an embodiment, for a coordinate system: an orthogonal rectangular coordinate system (x, y, z), a z-axis direction is consistent to a ray beam of a target center point, and a 0-reference plane is a bottom surface of the target (that is, a photon exit surface). A flight movement direction of the photons is expressed by using the rectangular coordinate system, a direction of the coordinate system is parallel to a coordinate system of the target, the photons use a projection $(p_x, p_y, p_z)$ of unit momentum direction in three coordinate directions to express a direction of the photons, and $p_x^2+p_y^2+p_z^2=1$. $p_z=1$ means that an emission direction of the photons is parallel to a central axis (vertical to a treatment plane) of the ray beam. $p_z=0$ means that the emission direction of the photons is horizontal emission on the 0-reference plane.

The photons in the embodiments of the disclosure are described according to the energy spectra. An energy width of each energy spectrum line is $Bin_E$. Each energy spectrum line is an energy group. The bremsstrahlung photons are divided into a plurality of energy groups, which are expressed as $E_i$, where i is a natural number, $E_i$ represents a median energy distribution of the ith group of photons, and an energy distribution width of the group of photons is $(E_i \pm \frac{1}{2} \cdot Bin_E)$. In a discretization energy spectrum, the photon source model functions of all energy bands have a unified form. Parameters in the function are highly related to energy heights, and are functions of energy. The source model functions of the discretization energy spectrum provide energy information of the photons.

The photon source model function of the medical linear accelerator in the disclosure includes a primary ray photon source model function and a scattered photon source model function, including:

First part: constructing the primary ray photon source model function (1) turning on the medical linear accelerator, bombarding an X-ray target of the medical linear accelerator using a generated high-energy electron beam, storing information, recorded on an initial phase space plane, of bremsstrahlung photons generated on a target plane in a first phase space file, and storing photon information, recorded on a phase space plane, of a therapeutic photon beam passing through a flattening filter in a second phase space file.

In order to acquire correct experimental data, a plane vertical to the central axis is required to be selected at an appropriate position on the central axis of the electron beam. All photon information passing through the plane is acquired through Monte Carlo simulation calculation, and includes fall point positions of the photons on the plane, a unit momentum component, energy, and a particle type. The plane is a phase space plane. A position of the phase space plane may be selected according to practical application requirements, which is not specifically limited in the disclosure.

The phase space plane is placed under the ray flattening filter, and close to a bottom end surface of the flattening filter. Two types of photon information are required to be recorded on the phase space plane. One type is the photon information of the initial bremsstrahlung photons, and the other type is the photon information of a therapeutic ray beam.

When a Monte Carlo method is used to record the photon information of the initial bremsstrahlung photons on an initial phase space plane, only component description of the tungsten target and the primary collimator of the accelerator is preserved, and component description of the flattening filter and the secondary collimator is removed; and when the Monte Carlo method is used to record the photon information of the therapeutic ray beam, component description of the tungsten target, the target substrate, the primary collimator and the flattening filter of the accelerator is preserved, and component description of the secondary collimator of the accelerator is removed.

It should be noted that, in the embodiments of the disclosure, a phase space file of bremsstrahlung photon information recorded on the initial phase space plane is denoted as a first phase space file. A phase space file of the therapeutic ray beam photon information recorded on the phase space plane is denoted as a second phase space file.

(2) converting the first phase space file and the second phase space file into phase space files which are respectively denoted as B-PhSp and R-PhSp on the target plane through photon reverse flight calculation; and separating photons recorded in the phase space file R-PhSp into primary ray photons and scattered ray photons, to obtain two new phase space files which are respectively denoted as p-PhSp and s-PhSp.

In order to unify the positions of the primary ray photon source model and the scattered photon source model to the plane (that is, a 0-reference plane) where the target plane of the accelerator is located, the two types of photons (that is, bremsstrahlung photons and therapeutic photon beam photons) recorded on the above two phase space planes are required to be processed by the photon reverse flight calculation. The first phase space file and the second phase space file are respectively converted to the 0-reference plane, so that two data files are correspondingly obtained. That is to say, the first phase space file is converted to the phase space file on the target plane, and denoted as the phase space file B-PhSp, and the second phase space file is converted to the phase space file on the target plane, and denoted as R-PhSp. According to the data file of the bremsstrahlung photons on the 0-reference plane, fluence distribution of the bremsstrahlung photons on the 0-reference plane can be obtained.

The photon data file of the therapeutic ray beam on the 0-reference plane includes primary ray photons and scattered ray photons, which need to be processed about primary and scattered rays, to acquire a fluence distribution map matrix of a primary ray photon beam on the 0-reference plane. The photons of the therapeutic ray beam recorded on the phase space plane include primary ray photons originating from the target plane of the accelerator and scattered ray photons generated in the flattening filter. After the primary ray photons and the scattered ray photons are separated, two new corresponding phase space files are obtained, which are respectively denoted as p-PhSp and s-PhSp.

In a preferred embodiment, separating photons recorded in the phase space file R-PhSp into primary ray photons and scattered ray photons specifically includes that:

in the photons recorded in the phase space file R-PhSp, photons of which position coordinates are located in a geometric projection area of a conical aperture of a primary collimator on a bottom end surface of the target are denoted as the primary ray photons, and the primary ray photons are able to return to the initial phase space plane along the aperture of the primary collimator; the photons outside the geometric projection area are denoted as the scattered ray photons, the originating position of the scattered ray photons is not on the target plane, but distributed in a larger range on the plane where the target is located, and the scattered ray photons cannot return to the initial phase space plane through the aperture of the primary collimator.

(3) constructing a bremsstrahlung photon fluence distribution function.

It should be noted that, the number of initial photons at any point on the 0-reference plane is proportional to the number of electrons bombarding the target point. The real electron beam is a two-dimensional Gaussian distribution with a certain full width at half maximum. The fluence distribution of the electron beam bombarding the target plane on a target incident surface is the two-dimensional Gaussian distribution. The full width at half maximum (FWHM) of electron distribution in a Gaussian function is known, which determines the size of a photon source of the accelerator, and can be derived from the information released by an accelerator manufacturer, or from a typical value recommended in the literature or the disclosure. A distribution standard deviation of the electron beam is $\delta = FWHM/2.335$. The energy of the electron beam is also a two-dimensional Gaussian distribution, which determines the energy spectrum and angular distribution characteristics of the bremsstrahlung photons. The yield of the initial bremsstrahlung photons generated at any point on the target plane is proportional to the number (that is, fluence) of electrons incident at the point. Therefore, the yield of the initial bremsstrahlung photons emitted on a bottom end surface of the X-ray target is a Gaussian distribution. A full width at half maximum of the Gaussian function equals a full width at half maximum of the fluence distribution of the electron beam bombarding the target.

In this way, a standard deviation S and a distribution function form of the fluence distribution of the bremsstrahlung photons generated by the target of the accelerator are known, which are two-dimensional Gaussian functions. A total count of the photons is determined by a total number of the photons required by simulation calculation. As shown in the following formula, the fluence distribution function of the initial bremsstrahlung photons generated at any point on the target plane can be expressed as follows:

$$N_B(x_s, y_s) = N_{B0} * e^{-\frac{x_s^2 + y_s^2}{2\sigma^2}};$$

$$\text{and } N_B = \int\int N_B(x_s, y_s) \cdot dx_s dy_s =$$

$$\int\int N_{B0} * e^{-\frac{x_s^2 + y_s^2}{2\sigma^2}} \cdot dx_s dy_s = N_{B0} \int\int e^{-\frac{x_s^2 + y_s^2}{2\sigma^2}} dx_s dy_s.$$

Where $\sigma$ is a distribution standard deviation; $(x_s, y_s)$ is coordinates of a certain point on the target plane, and a subscript s represents that the coordinates are on the target plane; and $N_{B0}$ is the photon fluence (yield) of a center point of the target plane, $N_B(x_s, y_s)$ is the photon fluence at any point $(x_s, y_s)$ on the target plane, a subscript B represents the bremsstrahlung photons, and subscript $B_0$ represents the photon count of the bremsstrahlung photons emitted at the center point of the target.

Then, after the energy spectrum is discretized, the fluence distribution function of the bremsstrahlung photons generated by the target plane of the X-ray target of the accelerator is shown as follows:

$$N_{B,E_i}(x_s, y_s) = \sum_i N_{B,E_i}(x_s, y_s) = P_{B,E_i} * N_B(x_s, y_s) = P_{B,E_i} \cdot N_{B0} * e^{-\frac{x_s^2 + y_s^2}{2\sigma^2}};$$

and, $$N_{B,E_i} =$$

$$\int\int N_{B,E_i}(x_s, y_s) * dx_s dy_s = \int\int P_{B,E_i} * N_B(x_s, y_s) * dx_s dy_s = P_{B,E_i} * N_B;$$

where $P_{B,E_i}$ is a branching ratio of $N_{B,E_i}(x_s, y_s)$ at $N_B(x_s, y_s)$, $N_{B,E_i}$ represents a total count of the bremsstrahlung photons of which energy is $E_i$, $N_B$ represents a total count of the bremsstrahlung photons of all energies, $N_{B0}$ represents the count of the bremsstrahlung photons generated at the center point of the target; and a subscript B is a bremsstrahlung identification, and E; is an energy identification of the ith spectral line.

(3) fitting the fluence distribution of the bremsstrahlung photons in the direction of the momentum component to obtain a fluence distribution function of the bremsstrahlung photons in the direction of the momentum component.

In a preferred embodiment, position coordinate parameters of the photons recorded in the phase space file B-PhSp are placed at a center point (0, 0, 0) of the target plane, wherein the target plane is set as the 0-reference plane.

In view of different energies, the total photons on the X-ray target are divided into a plurality of energy groups, for example, divided into 20 energy groups. The two-dimensional distribution lateral profile of the bremsstrahlung photons generated by each energy group on the 0-reference plane according to (x, y) is shown as FIG. 4. It can be learned that, the energy spectrum of electron fluence at any point on the target plane is the same. Therefore, the energy spectrum and the angular distribution characteristics of the initial bremsstrahlung photons generated at any point on the target plane are the same. Therefore, the position coordinates of all bremsstrahlung photons generated on the target plane are attributed to the center of the target plane, which is equivalent to the number of the bremsstrahlung photons generated at the center point of the target after the electron beam is increased by n times without changing the energy spectrum and the angular distribution characteristics of the initial bremsstrahlung photons at the center point of the target plane, and is equivalent to the effect that all the electron beams led out of the exit window of the accelerator bombard the center of the target. In this way, the efficiency of recording the number of the photons on the target plane can be effectively enhanced, thereby enhancing the working efficiency.

Therefore, the positions of all the bremsstrahlung photons generated on the target plane are placed to the center of the target plane to act as the fluence distribution of the bremsstrahlung photons at the center point of the target plane in a direction of a momentum component, and function fitting is performed, so that the photon probability distribution and function fitting of the bremsstrahlung photons in the direction of the momentum component are obtained. The probability distribution refers to the probability that the bremsstrahlung photons generated at the point are emitted in a certain direction. In this way, the photon probability distribution function of the bremsstrahlung photons generated at any point on the target plane in the direction of the momentum component is also the same.

Figure 1:
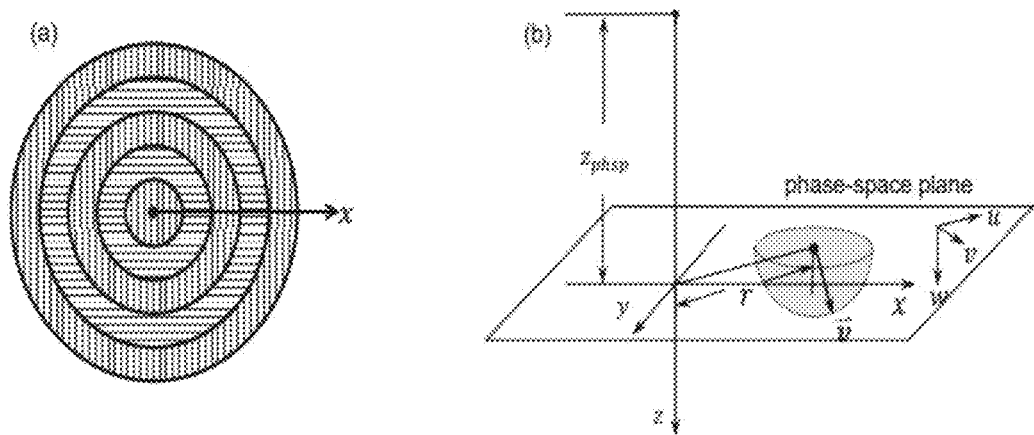
FIG. 1 shows a primary ray photon model during the establishment of an existing source model function, a shows a photon distribution ring formed on a phase space plane, and b shows a photon position and a momentum direction on the phase space plane.
Figure 2:
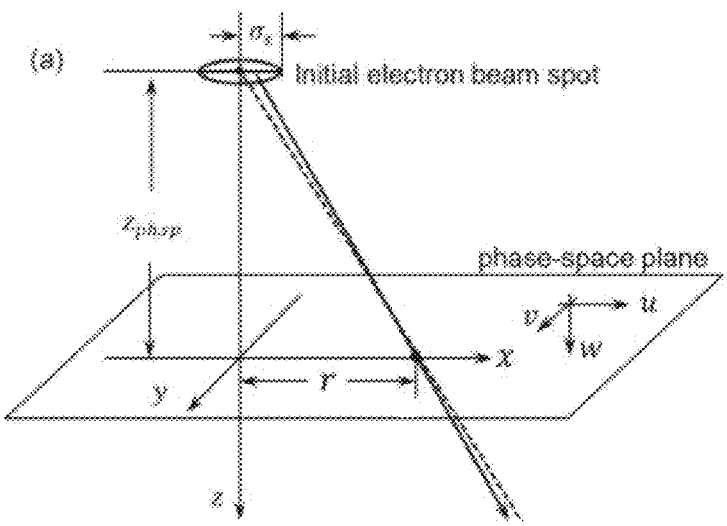
FIG. 2 is a schematic geometric diagram of a primary ray photon model during the establishment of an existing source model function.
Figure 3:
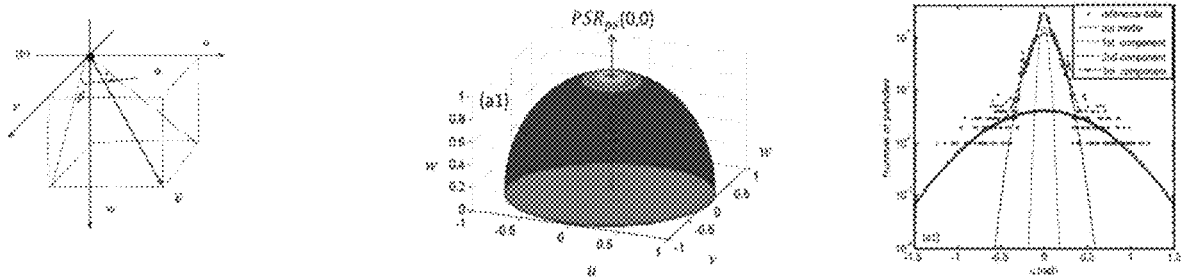
FIG. 3 is a distribution diagram of scattered photons on a spherical surface after the scattered photons are grouped according to momentum distribution in an existing source model function.
Figure 4:
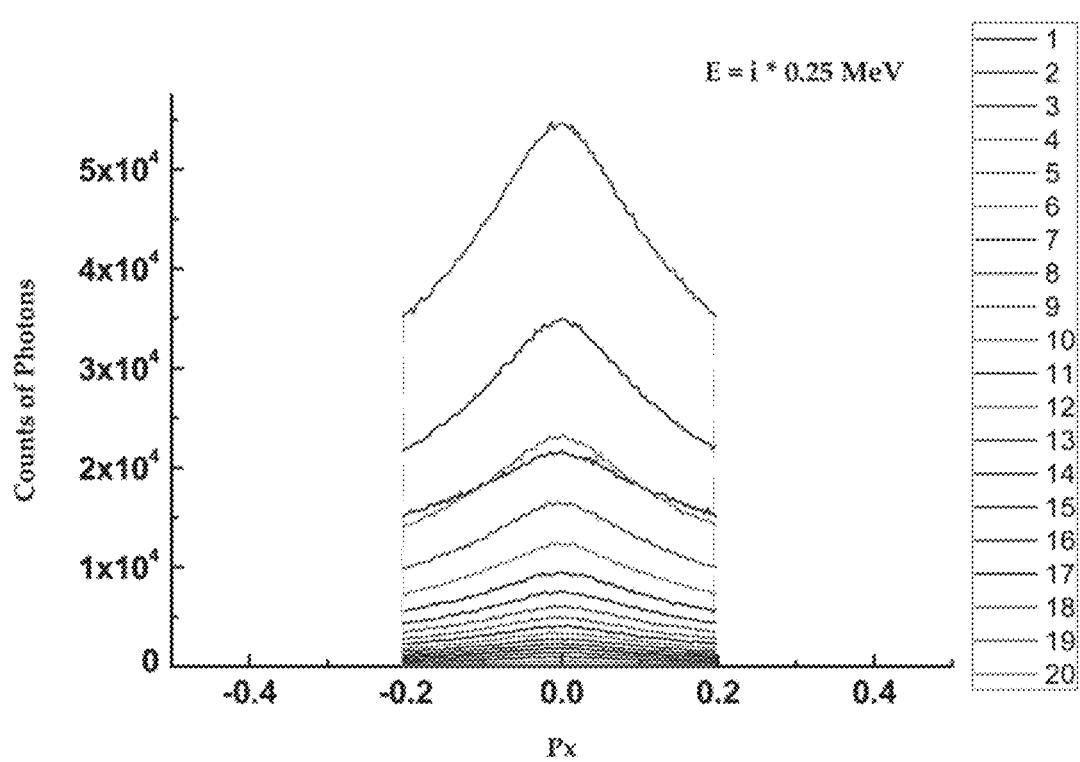
FIG. 4 is a lateral profile of angular momentum distribution of bremsstrahlung photons according to an embodiment of the disclosure.

Therefore, the fluence distribution of the bremsstrahlung photons in the direction of the momentum component is acquired, and as shown in FIG. 4, the fitting function is shown as follows:

$$N'_{B,E_i}(p_x, p_y) = a'_{E_i,1} * e^{-\frac{p_x^2 + p_y^2}{2\sigma^2_{B,E_i,m_1}}} + a'_{E_i,2} * e^{-\frac{p_x^2 + p_y^2}{2\sigma^2_{B,E_i,m_2}}};$$

wherein $N'_{B,E_i}(p_x, p_y)$ represents the fluence distribution of the bremsstrahlung photons in the ith energy group generated in the center point of the target in the direction of the momentum component; $\sigma_{B,E_i,m_1}$ and $\sigma_{B,E_i,m_2}$ are fluence distribution standard deviations of the photons of which energy is $E_i$ in the bremsstrahlung photons in the direction of the momentum component, $a'_{E_i,1}$ and $a'_{E_i,2}$ are coefficients of a function expression, which equal to the count of the bremsstrahlung photons emitted at an angle of 0 degree, a flight momentum direction of the bremsstrahlung photons is expressed by a projection value of a unit momentum on a three-dimensional rectangular coordinate system, that is, $(p_x, p_y, p_z)$, and $p_x^2 + p_y^2 + p_z^2 = 1$.

Wherein B represents the bremsstrahlung photons, $E_i$ represents the energy of the ith spectral line, m represents the momentum, that is, $\sigma_{B,E_i,m_1}$ and $\sigma_{B,E_i,m_2}$ are two standard deviations of momentum distribution.

(4) obtaining a fluence probability distribution function according to the fluence distribution function of the bremsstrahlung photons emitted from the fluence point on the target plane in the momentum component.

Since angular fluence probabilities of the bremsstrahlung photons generated by all fluence points on the target plane are the same, the fluence distribution function of the bremsstrahlung photons emitted from the fluence point on the target plane in the momentum component is fitted, to obtain the fluence probability distribution function of the bremsstrahlung photons emitted from the fluence point on the target plane in the momentum component, which is shown as follows:

$$P'_{B,E_i}(p_x, p_y) = \frac{N'_{B,E_i}(p_x, p_y)}{\iint N'_{B,E_i}(p_x, p_y) \cdot dp_x dp_y} = a_{E_i,1} * e^{-\frac{p_x^2+p_y^2}{2\sigma^2_{B,E_i,m_1}}} + a_{E_i,2} * e^{-\frac{p_x^2+p_y^2}{2\sigma^2_{B,E_i,m_2}}};$$

wherein $a_{E_i,1}$ and $a_{E_i,2}$ are coefficients of a fluence probability distribution function expression of the bremsstrahlung photons in the direction of the momentum component, which are obtained according to normalization calculation of $a'_{E_i,1}$ ad $a'_{E_i,2}$.

(5) obtaining the fluence distribution of the bremsstrahlung photons absorbed by the flattening filter in the direction of the momentum component according to a difference between the fluence distribution of the bremsstrahlung photons in the direction of the momentum component and the fluence distribution of the primary ray photons in the direction of the momentum component, and obtaining a fluence distribution function of the bremsstrahlung photons absorbed by the flattening filter in the direction of momentum component through fitting.

Figure 5:
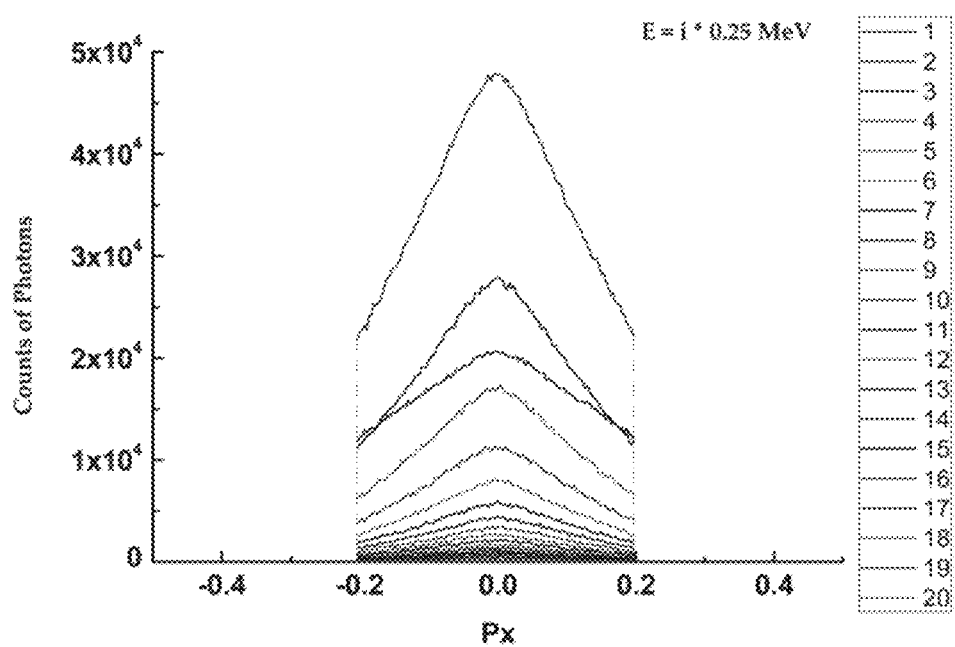
FIG. 5 is a lateral profile of angular momentum distribution of photons absorbed by a flattening filter on a target plane according to an embodiment of the disclosure.
Figure 6:
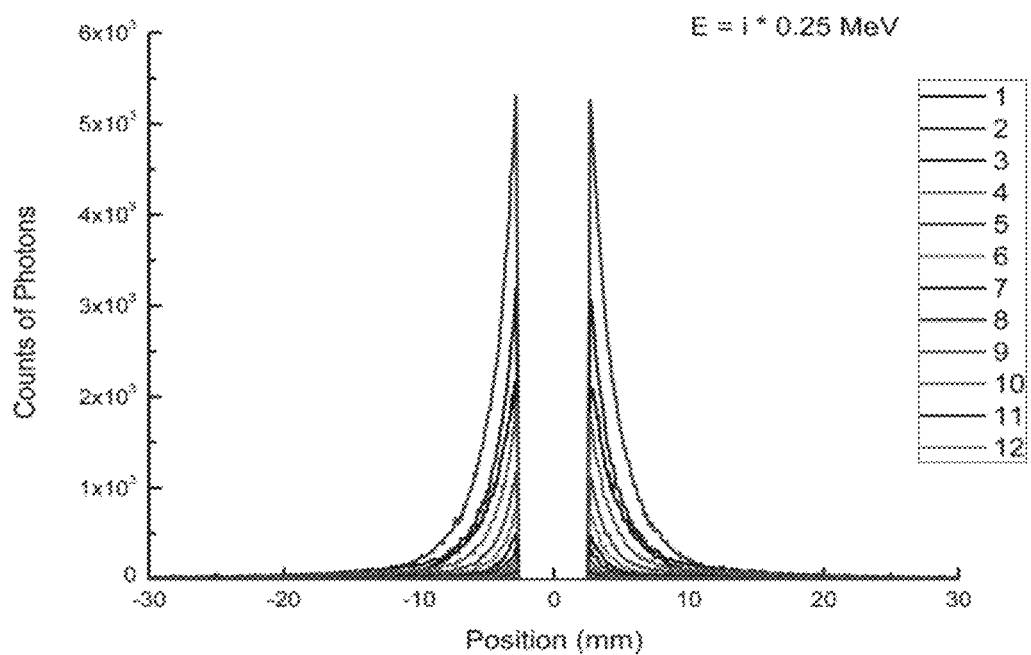
FIG. 6 is a lateral profile of spatial fluence distribution of scattered photons on a target plane according to an embodiment of the disclosure.
Figure 7:
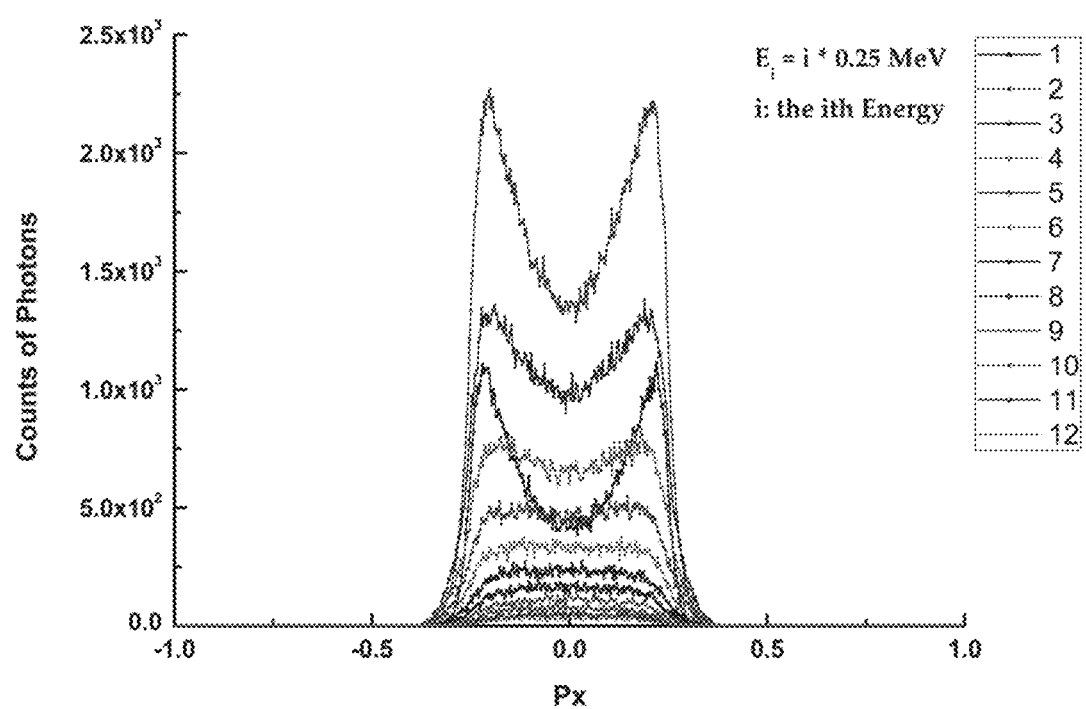
FIG. 7 is a lateral profile of angular momentum distribution of scattered photons on a target plane according to an embodiment of the disclosure.
Figure 8:
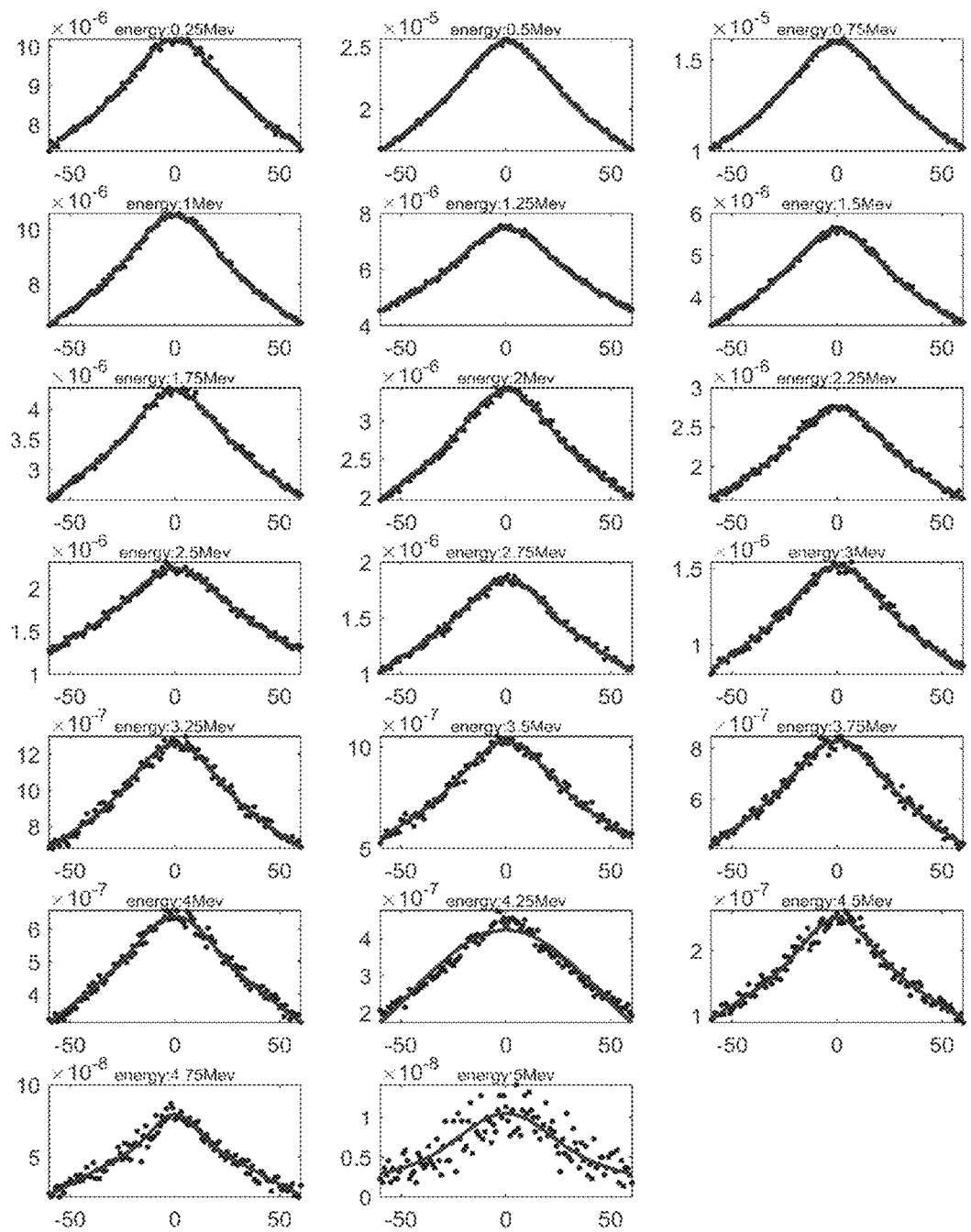
FIG. 8 is a lateral profile of comparison between fluence probability distribution of bremsstrahlung photons in a momentum component and calculation results of a model function according to an embodiment of the disclosure.
Figure 9:
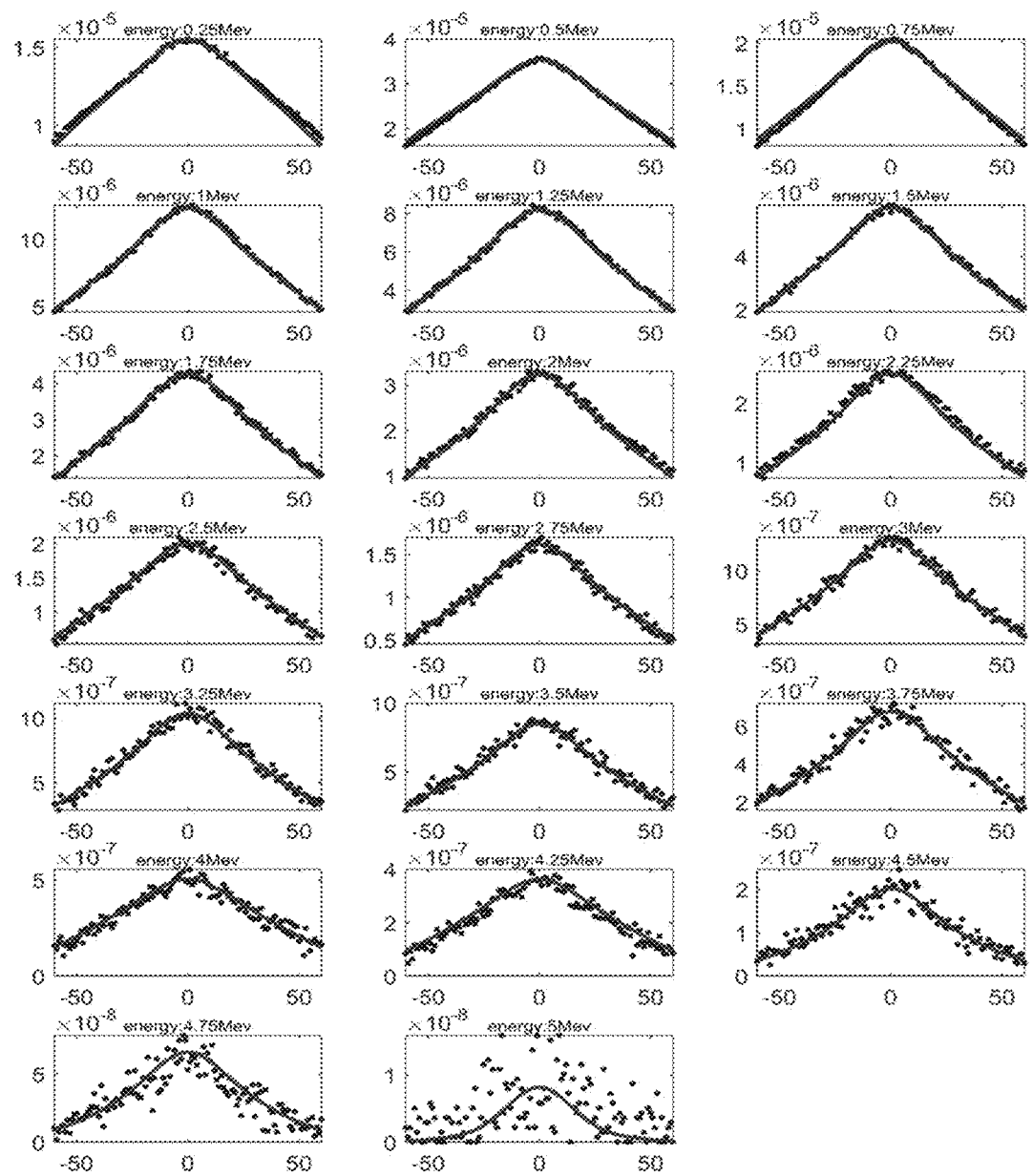
FIG. 9 shows a comparison between fluence probability distribution of bremsstrahlung photons absorbed by a flattening filter in a momentum component and calculation results of a model function according to an embodiment of the disclosure.
Figure 10:
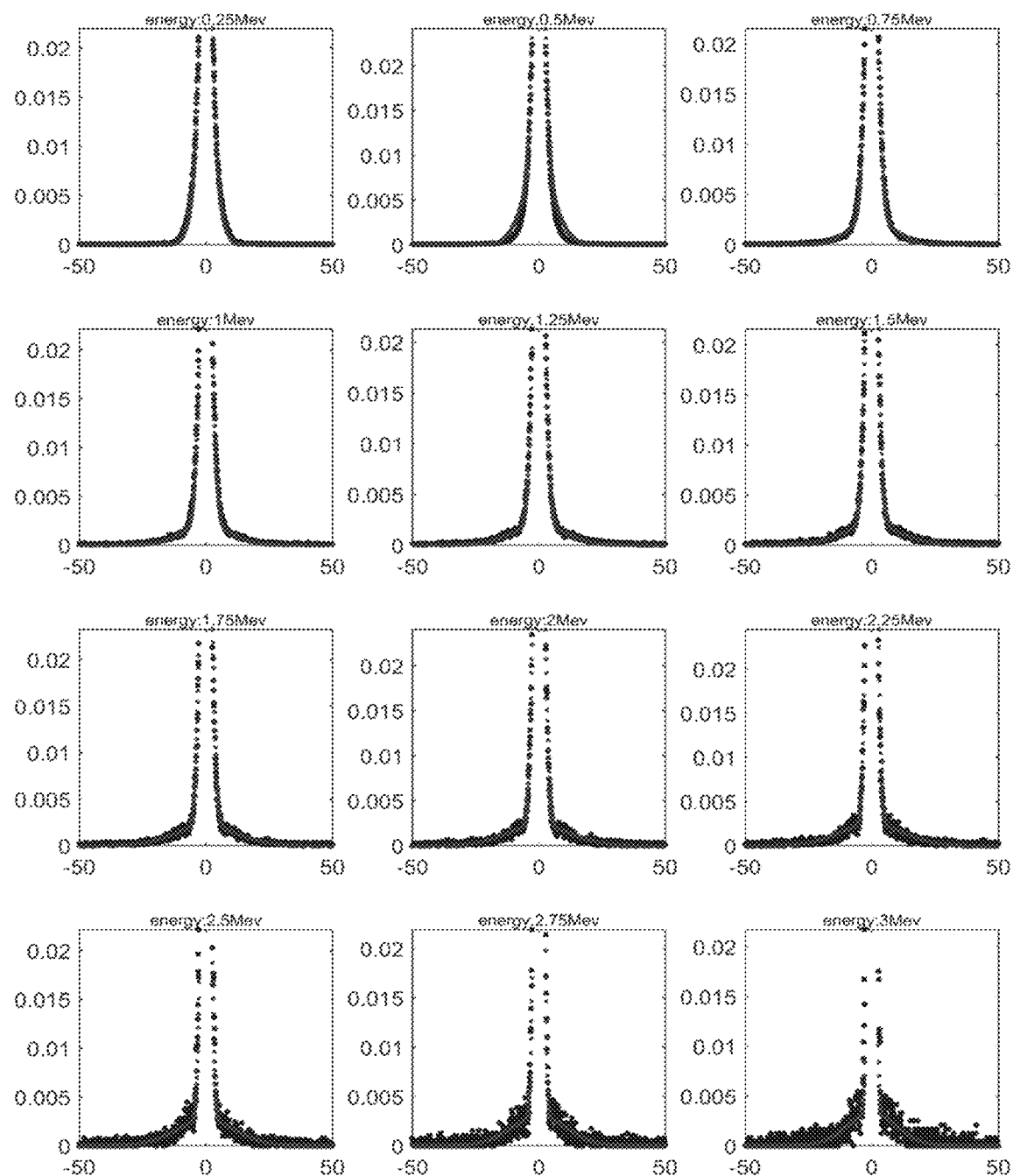
FIG. 10 shows a comparison between spatial fluence distribution of scattered photons on a 0-reference plane and calculation results of a model function according to an embodiment of the disclosure.
Figure 11:
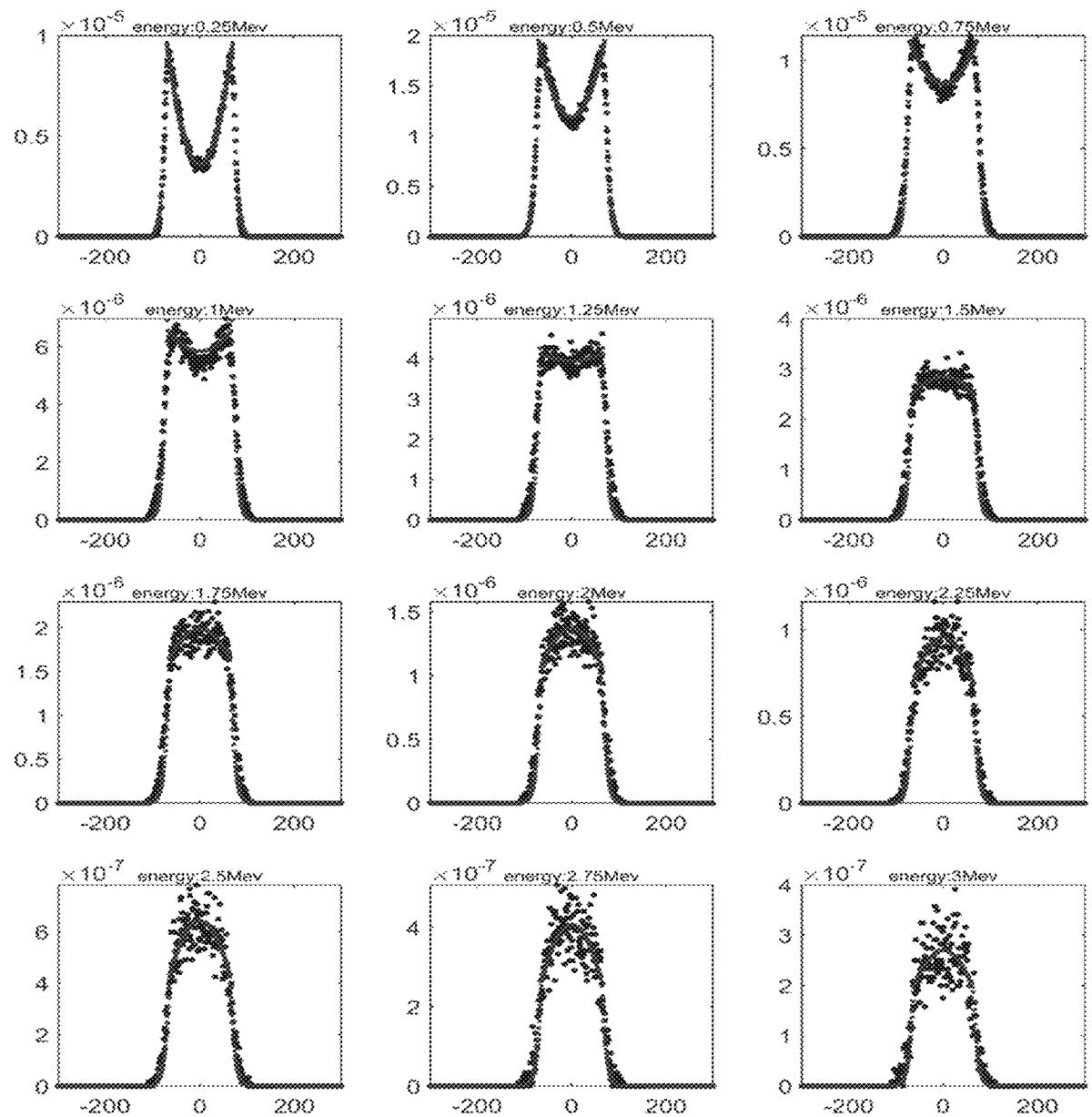
FIG. 11 shows a comparison between fluence probability distribution of scattered photons in a momentum component and calculation results of a model function according to an embodiment of the disclosure.
Figure 12:
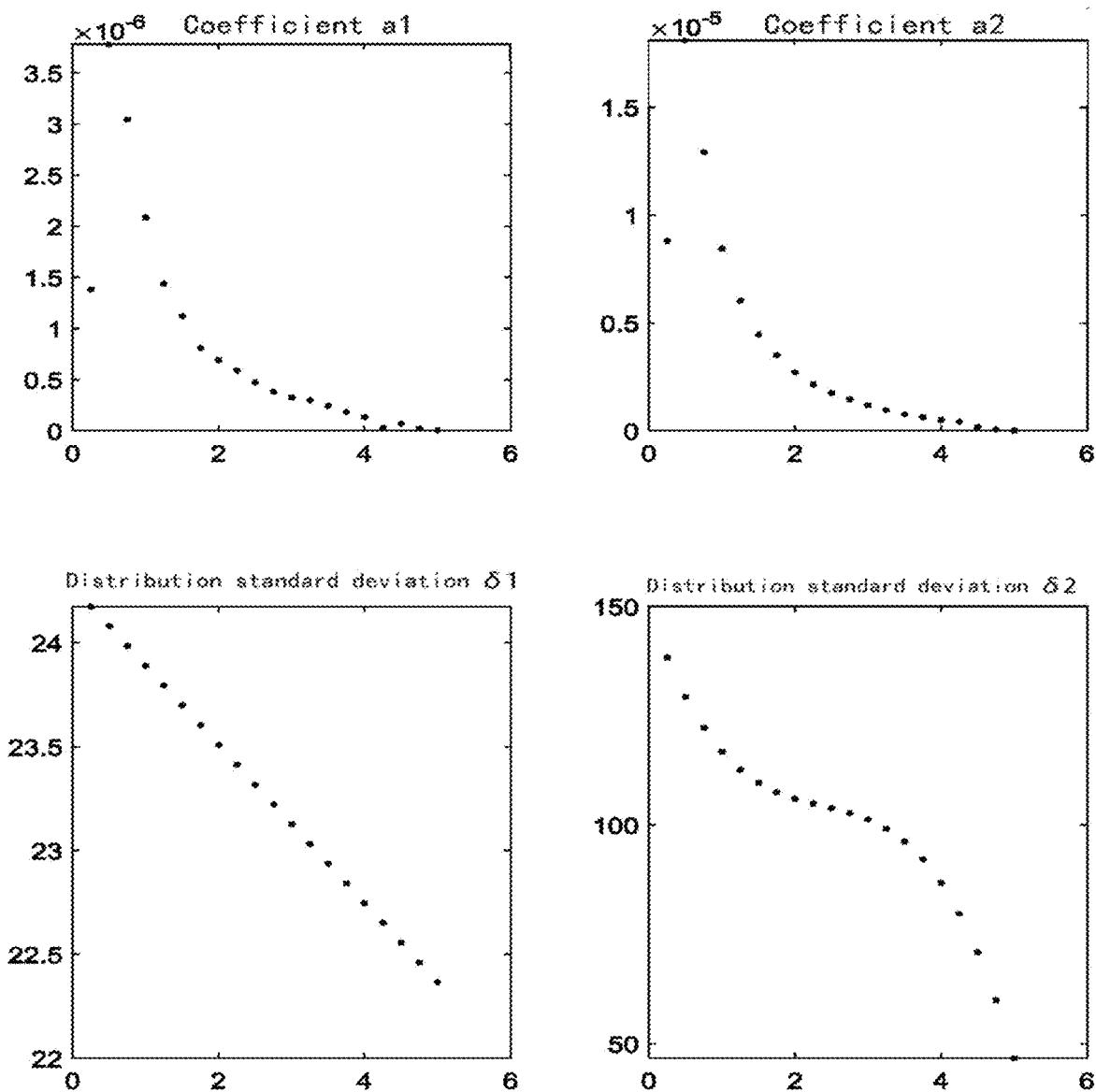
FIG. 12 shows a relationship between a coefficient and standard deviation of a model function of initial bremsstrahlung photons distributed in a direction of a momentum component and photon energy according to an embodiment of the disclosure.
Figure 13:
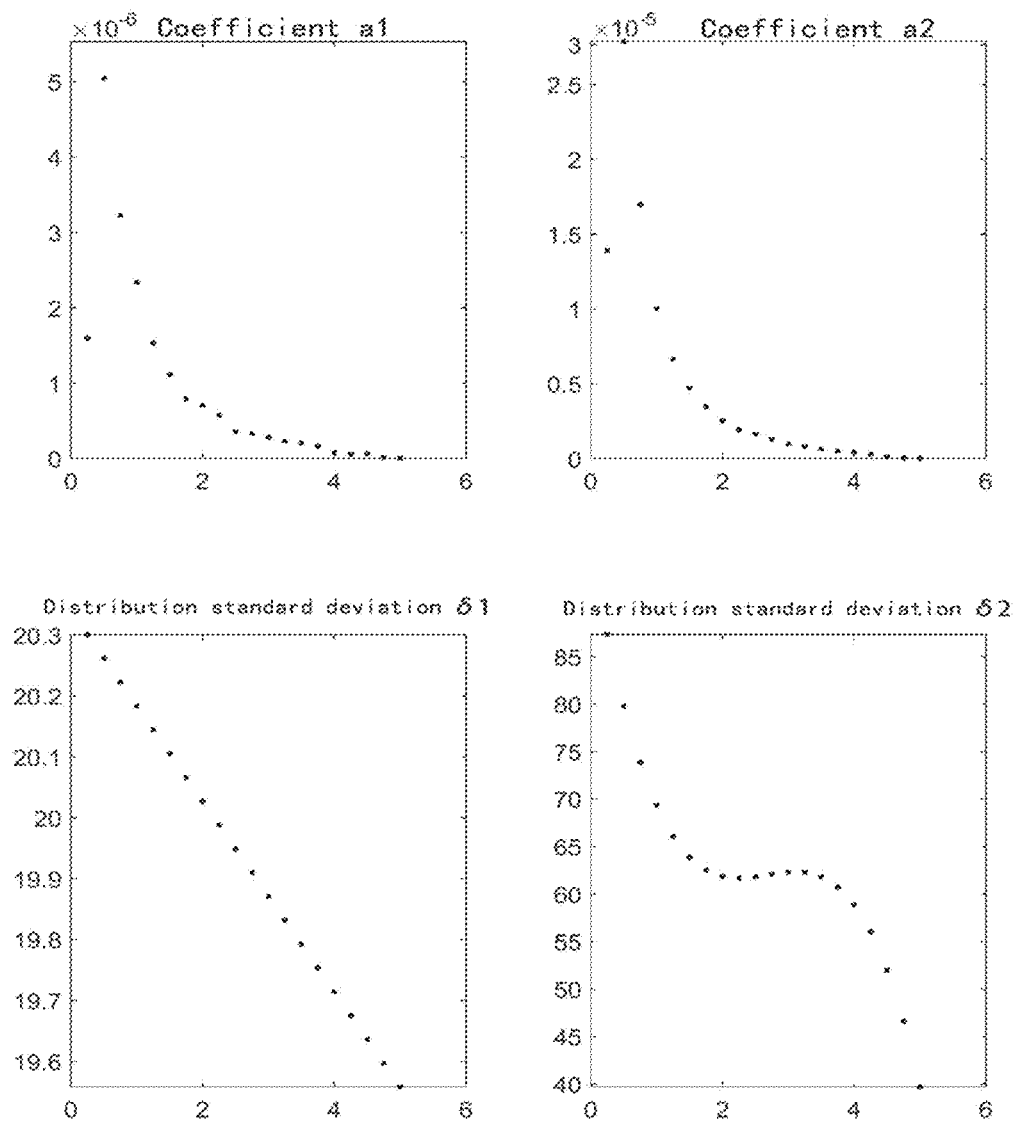
FIG. 13 shows a relationship between a coefficient and standard deviation of a model function of bremsstrahlung photons absorbed by a flattening filter and distributed in a direction of a momentum component and photon energy according to an embodiment of the disclosure.
Figure 14:
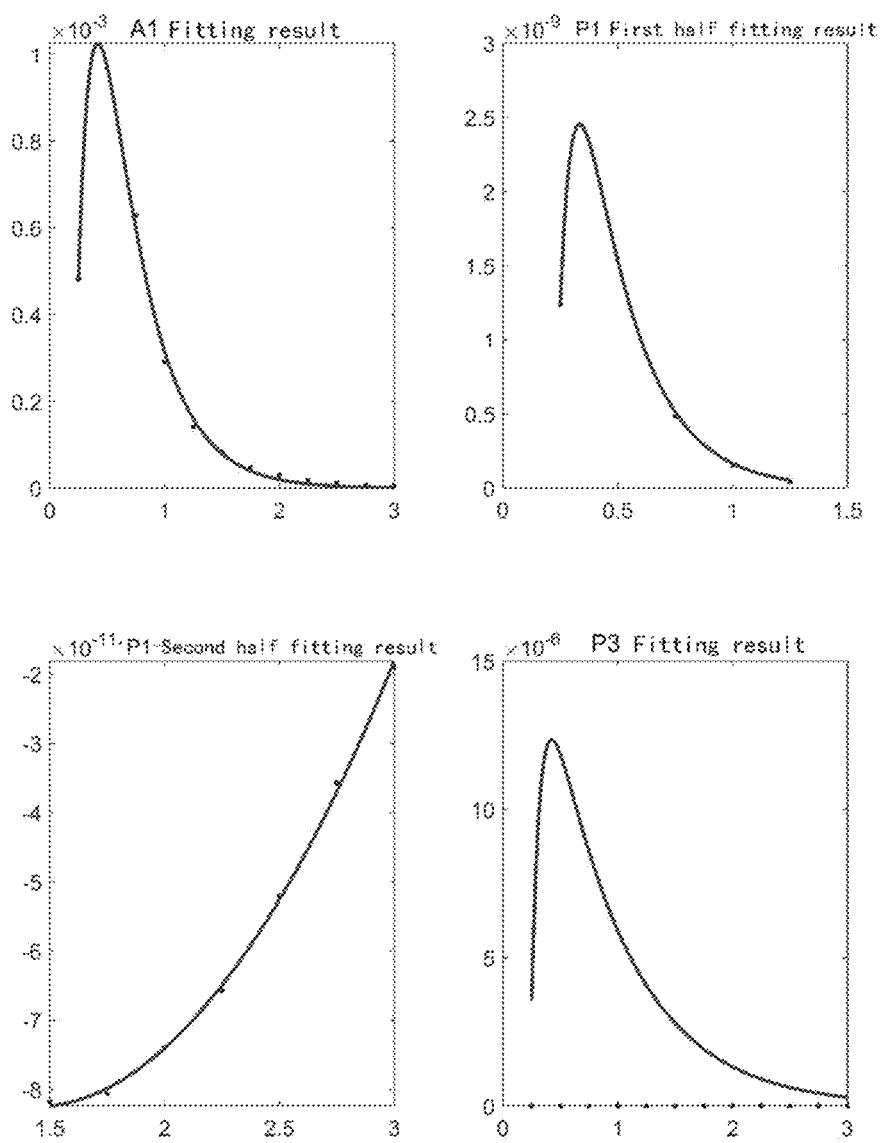
FIG. 14 shows a relationship between a coefficient of a scattered photon source model function and photon energy according to an embodiment of the disclosure.

The photon position coordinates recorded in the phase space file B-PhSp of the bremsstrahlung photons and the phase space file of the primary ray photons are placed at the target center (0, 0, 0), to respectively obtain the fluence distribution of the bremsstrahlung photons in the direction of momentum component and the fluence distribution B-map (as shown in FIG. 4) and p-map of the primary ray photons in the direction of momentum component. A difference between the fluence distribution of the bremsstrahlung photons in the direction of the momentum component and the fluence distribution of the primary ray photons in the direction of the momentum component is the fluence distribution of the bremsstrahlung photons absorbed by the flattening filter in the direction of the momentum component, as shown in FIG. 5.

Function fitting is performed on the fluence distribution of the bremsstrahlung photons absorbed by the flattening filter in the direction of the momentum component, to obtain the fluence distribution function of the bremsstrahlung photons absorbed by the flattening filter in the direction of momentum component, which is shown as follows:

$$N'_{(f-absorbed),E_i}(p_x, p_y) = b'_{E_i,1} * e^{-\frac{p_x^2+p_y^2}{2\sigma^2_{(f-absorbed),E_i,m_1}}} + b'_{E_i,2} * e^{-\frac{p_x^2+p_y^2}{2\sigma^2_{(f-absorbed),E_i,m_2}}};$$

wherein $N'_{(f-absorbed),E_i}(p_x,p_y)$ represents fluence distribution of the bremsstrahlung photons absorbed by the flattening filter and with the energy of the ith spectral line in the direction of momentum component $(p_x,p_y)$; $\sigma_{(f-absorbed),E_i,m_1}$ and $\sigma_{(f-absorbed),E_i,m_2}$ are respectively standard deviations of the above two two-dimensional Gaussian functions; and $b'_{E_i,1}$ and $b'_{E_i,2}$ are respectively coefficients of the above two Gaussian function expressions.

(6) mathematically normalizing the total count of the bremsstrahlung photons with the energy of the ith spectral line at any fluence point, to obtain a fluence probability distribution function of the bremsstrahlung photons emitted from any fluence point on the target plane and absorbed by the flattening filter in the direction of momentum component, which is shown as follows:

$$P'_{(f-absorbed),E_i},(p_x, p_y)] = \frac{N'_{(f-absorbed),E_i}(p_x, p_y)}{\iint_{-m}^{m} N'_{(f-absorbed),E_i}(p_x, p_y)dp_x dp_y} =$$

$$b_{E_i,1} * e^{-\frac{p_x^2+p_y^2}{2\sigma^2_{(f-absorbed),E_i,m_1}}} + b_{E_i,2} * e^{-\frac{p_x^2+p_y^2}{2\sigma^2_{(f-absorbed),E_i,m_2}}};$$

wherein $P'_{(f-absorbed),E_i}(p_x,p_y)$ is the Probability of the bremsstrahlung photons absorbed by the flattening filter; and $b_{E_i,1}$ and $b_{E_i,2}$ are respectively two coefficients of a probability distribution model function, and obtained through mathematical normalization calculation of $b'_{E_i,1}$ and $b'_{E_i,2}$.

(7) constructing a primary ray photon source model function.

It should be noted that, the fluence distribution function of the bremsstrahlung photons emitted by the target of the accelerator provides coordinate position information $(x_s, y_s, z_s)$ and yield information $N_B(x_s, y_s)$ of photon emission points. A difference between the fluence probability distribution function of the bremsstrahlung photons emitted from the fluence point on the target plane in the momentum component and the fluence probability distribution function of the bremsstrahlung photons emitted from the fluence point on the target plane and absorbed by the flattening filter in the direction of momentum component is the fluence probability of the primary ray photons emitted from the fluence point in the momentum component, which provides information $(p_x, p_y, p_z)$ about the momentum direction of the photons and the appearance probability of the photons.

The fluence probability distribution function of the primary ray photons emitted by the fluence point on the target plane is obtained according to a difference between the fluence probability distribution function of the bremsstrahlung photons emitted from the fluence point on the target plane in the momentum component and the fluence probability distribution function of the bremsstrahlung photons emitted from the fluence point on the target plane and absorbed by the flattening filter in the direction of momentum component, and by combining the fluence distribution function of the bremsstrahlung photons, the primary ray photon source model function is obtained, which is shown as follows:

$$N_{E_i}(x_s, y_s, p_x, p_y) = N_{B,E_i}(x_s, y_s) * \left[ P'_{B,E_i}(p_x, p_y) - P'_{(f-absorbed),E_i}(p_x, p_y) \right];$$

wherein: $N_{B,E_i}(x_s, y_s) =$ $$N_{B,E_i,0} * e^{-\frac{x_s^2+y_s^2}{2\delta^2}} = P_{B,E_i} * N_{B0} * e^{-\frac{x_s^2+y_s^2}{2\delta^2}} = P_{B,E_i} * N_B(x_s, y_s);$$

and $$P'_{B,E_i}(p_x, p_y) =$$

$$\frac{N'_{B,E_i}(p_x, p_y)}{\iint N'_{B,E_i}(p_x, p_y) \cdot dp_x dp_y} = a_{E_i,1} * e^{-\frac{p_x^2+p_y^2}{2\sigma_{B,E_i,m_1}^2}} + a_{E_i,2} * e^{-\frac{p_x^2+p_y^2}{2\sigma_{B,E_i,m_2}^2}};$$

and $$P'_{(f-absorbed),E_i,}(p_x, p_y)] = \frac{N'_{(f-absorbed),E_i}(p_x, p_y)}{\iint_{-m}^{m} N'_{(f-absorbed),E_i}(p_x, p_y) dp_x dp_y} =$$

$$b_{E_i,1} * e^{-\frac{p_x^2+p_y^2}{2\sigma_{(f-absorbed),E_i,m_1}^2}} + b_{E_i,2} * e^{-\frac{p_x^2+p_y^2}{2\sigma_{(f-absorbed),E_i,m_2}^2}};$$

wherein the primary ray photon source model is located on the 0-reference plane, the flight momentum direction of the primary ray photons is expressed by the projection value of the unit momentum on the three-dimensional rectangular coordinate system, that is, ($p_x$, $p_y$, $p_z$), and $p_x^2+p_y^2+p_z^2=1$, therefore, $z_s$ and $p_z$ are omitted.

Each parameter in the above function expression is given in a process of fitting the function, and $P'_{B,E_i}(p_x,p_y)$ represents the fluence probability distribution of the bremsstrahlung photons in the momentum component; $P'_{(f-absorbed),E_i}(p_x,p_y)$ is the probability of the bremsstrahlung photons absorbed by the flattening filter; $a_{E_i,1}$ and $a_{E_i,2}$ are coefficients of the fluence probability distribution function of the bremsstrahlung photons in the momentum component, and $\sigma_{B,E_i,m1}$ and $\sigma_{B,E_i,m2}$ are the distribution standard deviations of the fluence probability distribution function of the bremsstrahlung photons in the momentum component; and $b_{E_i,1}$ and $b_{E_i,2}$ are coefficients of the fluence probability function of the bremsstrahlung photons in the momentum component, $\sigma_{(f-absorbed)E_i,m1}$ and $\sigma_{(f-absorbed)E_i,m1}$ are standard deviations of the probability function of the bremsstrahlung photons absorbed by the flattening filter, and (f-absorbed) is an identification indicating being absorbed by the flattening filter.

It should be noted that, the primary ray photon source model in the therapeutic ray beam of the medical linear accelerator is a function related to the photon information parameters $x_s$, $y_s$, $z_s$, $p_x$, $p_y$, $p_z$ and $E_i$. A standard deviation $\sigma$ of the fluence distribution of the bremsstrahlung photons generated on the target plane is known. Parameters $\sigma_{B,E_i,m_1}$, $\sigma_{B,E_i,m_2}$, $\sigma_{(f-absorbed),E_i,m_1}$, and $\sigma_{(f-absorbed),E_i,m_2}$ in the model function are given in the fitting function. Since the position height of the target plane of the accelerator is a known fixed value. Therefore, the writing of $z_s$ can be omitted. In addition, a flight movement direction of the photons is expressed by using the rectangular coordinate system, a direction of the coordinate system is parallel to a coordinate system of the target, the photons use a projection ($p_x$,$p_y$,$p_z$) of unit momentum direction in three coordinate directions to express a direction of the photons, and $p_x^2+p_y^2+p_z^2=1$. $p_z=1$ means that an emission direction of the photons is parallel to a central axis (vertical to a treatment plane) of the ray beam. $p_z=0$ means that the emission direction of the photons is horizontal emission on the 0-reference plane. In this way, the writing of $p_z$ may also be omitted.

For the primary ray photons in the therapeutic photon beam of the accelerator, a definitional domain of $x_s$, $y_s$ meets: $x_s^2+y_s^2 \leq (\emptyset/2)^2$, that is, the geometry size of a photon source. The emission points of the primary ray photons described in the model are on the source.

Second Part: Constructing the Scattered Photon Source Model Function

A complete scattered ray photon source model function includes two constituent parts, that is, a fluence distribution function of the scattered photons on the 0-reference plane and a photon fluence probability distribution function of the scattered photons emitted from a certain fluence point, which jointly construct the scattered photon source model function.

The method specifically includes the following steps.

(1) fitting the fluence distribution of the scattered photons on the 0-reference plane to obtain the fluence distribution function of the scattered photons.

It should be noted that, a distribution area of the scattered photons recorded in the phase space file s-PhSp of the scattered photons is discretized to form a pixel grid. The fluence distribution of the scattered photons on the 0-reference plane is acquired in a unit of the pixel grid. Fitting is performed on the fluence distribution of the scattered photons by using a double gaussian function polynomial to obtain a fluence distribution function of the scattered photons, which is shown as follows:

$$N_{scatter,E_i}(x_s, y_s) = a_i * e^{-\frac{x_s^2+y_s^2}{2\sigma_{s,E_i,1}^2}} + b_i * e^{-\frac{x_s^2+y_s^2}{2\sigma_{s,E_i,2}^2}};$$

wherein ($x_s$, $y_s$) is position coordinates of any point on the 0-reference plane, $N_{scatter,E_i}(x_s, y_s)$ represents the number of the scattered photons at the fluence point ($x_s$, $y_s$), $a_i$ and $b_i$ are coefficients of a fitting function of the fluence distribution of the scattered photons of which energy is $E_i$; $\sigma_{s,E_i,1}$ and $\sigma_{s,E_i,2}$ are distribution standard deviations of the fitting function of the fluence distribution of the scattered photons of which energy is $E_i$; and s in a parameter subscript represents a scattered ray identification.

(2) obtaining an average fluence probability distribution function of the scattered photons in the momentum component according to the fluence distribution function of the scattered photons emitted from each fluence point on the target plane in the momentum component.

Since the fluence probability distribution of the scattered photons at each fluence point on the 0-reference plane in the direction of the momentum component is slightly anisotropic, in the embodiments of the disclosure, an average of the fluence probability distribution of a plurality of fluence points is used as the representative of the fluence probability of the scattered photons of each fluence point in the direction of the momentum component, and such an approximate method does not affect the accuracy and precision of the model.

Therefore, the fitting function of the fluence distribution of the scattered photons emitted from each fluence point on the target plane in the momentum component is shown as follows:

$$N_{scatter,E_i}(p_x, p_y) = \begin{cases} a'_i * e^{-\frac{p_x^2+p_y^2}{2\sigma_{s,E_i,m1}^2}} + b'_i * e^{-\frac{p_x^2+p_y^2}{2\sigma_{s,E_i,m2}^2}}; & \text{function variable domain: } p_x^2 + p_y^2 > r^2 \\ c'_i * (p_x^2 + p_y^2) + d'_i; & \text{function variable domain: } p_x^2 + p_y^2 \leq r^2 \end{cases}$$

wherein parameters $a'_i$, $b'_i$, $c'_i$ and $d'_i$ are coefficients of the fitting function of the fluence distribution in the momentum component; and $\sigma_{s,E_i,m1}^2$ and $\sigma_{E_i,m2}$ are standard deviations of the fitting function of the fluence distribution in the momentum component. In a subscript of each parameter, i represents an identification of an energy group of the ith spectral line.

Then, an average fluence probability distribution function of the scattered photons in the momentum component is obtained according to the fluence distribution function of the scattered photons in the momentum component, which is shown as follows:

$$P'_{scatter,E_i}(p_x, p_y) = \begin{cases} a_i * e^{-\frac{p_x^2+p_y^2}{2\sigma_{s,E_i,m1}^2}} + b_i * e^{-\frac{p_x^2+p_y^2}{2\sigma_{s,E_i,m2}^2}}; & \text{function variable domain: } p_x^2 + p_y^2 > r^2 \\ c_i * (p_x^2 + p_y^2) + d_i; & \text{function variable domain: } p_x^2 + p_y^2 \leq r^2 \end{cases}$$

wherein a function domain r is given by using the following mathematical method:

$$a_i * e^{-\frac{r^2}{2\sigma_{s,E_i,m1}^2}} + b_i * e^{-\frac{r^2}{2\sigma_{s,E_i,m2}^2}} = c_i * r^2 + d_i;$$

the parameters $a_i$, $b_i$, $c_i$, $d_i$, $\sigma_{s,E_i,m1}$ and $\sigma_{s,E_i,2}$ in the average fluence probability distribution function of the scattered photons in the momentum component are given by a fitting process, wherein $a_i$, $b_i$, $c_i$ and $d_i$ are coefficients of the function, $\sigma_{s,E_i,m1}$ and $\sigma_{s,E_i,m2}$ are distribution standard deviations distributed along the momentum, these parameters are closely related to energy, and are able to be fitted to the energy to respectively form a relationship function between each parameter and the energy. The lowercase letter in the parameter subscript is the scattered photon identification, and the other subscripts have the same meaning as above.

(3) constructing the scattered photon source model function according to the fluence distribution function of the scattered photons and the average fluence probability distribution function of the scattered photons emitted by all fluence points on the plane on which the target is located in the momentum component is shown as follows:

$N_{scatter,E_i}(x_s,y_s,z_s,p_x,p_y,p_z,E_i) = N_{scatter,E_i}(x_s,y_s,z_s) * P'_{scatter,E_i}(p_x,p_y,p_z).$ The above fluence distribution function of the scattered photons provides initial coordinates ($x_s,y_s,z_s$) of the photons in a scattered photon source and the count $N_{scatter}(x_s,y_s)$ of the scattered photons of the fluence point. The fluence probability distribution function of the scattered photons in the momentum component provides momentum direction information ($p_x,p_y,p_z$) and probability of the scattered photons emitted from the fluence point.

The embodiments of the disclosure are described in detail above. Detailed examples are used in this description to describe the principles and implementations of the disclosure. The description of the above embodiments is merely used to facilitate understanding of the core idea of the disclosure. In addition, for those of ordinary skill in the art, according to the idea of the disclosure, there will be changes in the specific implementations and the scope of application. In summary, the content of this description should not be construed as a limitation of the disclosure.

What is claimed is:

1. A method for constructing a photon source model function of a medical linear accelerator, wherein a photon source model of the medical linear accelerator comprises a primary ray photon source model and a scattered ray photon source model, and the method comprises:

turning on the medical linear accelerator, bombarding an X-ray target of the medical linear accelerator using a generated high-energy electron beam, storing information, recorded on an initial phase space plane, of bremsstrahlung photons generated on a target plane in a first phase space file, and storing photon information, recorded on a phase space plane, of a therapeutic photon beam passing through a flattening filter in a second phase space file;

converting the first phase space file and the second phase space file into phase space files which are respectively denoted as B-PhSp and R-PhSp on the target plane through photon reverse flight calculation, and separating photons recorded in the phase space file R-PhSp into primary ray photons and scattered ray photons to obtain two new phase space files which are respectively denoted as p-PhSp and s-PhSp;

constructing a primary ray photon source model function according to the fluence distribution function of the bremsstrahlung photon, a fluence probability distribution function of bremsstrahlung photons emitted from a fluence point on the target plane in a momentum component, and a fluence probability distribution function of the bremsstrahlung photons emitted from the fluence point on the target plane and absorbed by the flattening filter in a direction of the momentum component; and constructing a scattered ray photon source model function according to the fluence distribution function of the scattered ray photon and an average fluence probability distribution function of scattered photons emitted by all fluence points on a plane on which the target is located in the momentum component.

2. The method for constructing a photon source model function of a medical linear accelerator according to claim 1, wherein separating photons recorded in the phase space file R-PhSp into primary ray photons and scattered ray photons specifically comprises: in the photons recorded in the phase space file R-PhSp, denoting photons of which position coordinates are located in a geometric projection area of a conical aperture of a primary collimator on a bottom end surface of the target as primary ray photons, the primary ray photons being able to return to the initial phase space plane along the aperture of the primary collimator; and denoting photons outside the geometric projection area as scattered ray photons.

3. The method for constructing a photon source model function of a medical linear accelerator according to claim 2, wherein position coordinate parameters of the photons recorded in the phase space file B-PhSp and the phase space file p-PhSp are placed at a center point (0, 0, 0) of the target plane, wherein the target plane is set as a 0-reference plane.

4. The method for constructing a photon source model function of a medical linear accelerator according to claim 3, wherein the bremsstrahlung photons of a continuous energy spectrum are divided into a plurality of energy groups which are represented by $E_i$ by using an energy width $Bin_E$, wherein i is a natural number and represents a median energy distribution of the ith group of photons, and an energy distribution width of the group of photons is $$\left(E_i \pm \frac{1}{2} \cdot Bin_E\right).$$

5. The method for constructing a photon source model function of a medical linear accelerator according to claim 1, wherein position coordinate parameters of the photons recorded in the phase space file B-PhSp and the phase space file p-PhSp are placed at a center point (0, 0, 0) of the target plane, wherein the target plane is set as a 0-reference plane.

6. The method for constructing a photon source model function of a medical linear accelerator according to claim 5, wherein the bremsstrahlung photons of a continuous energy spectrum are divided into a plurality of energy groups which are represented by $E_i$ by using an energy width $Bin_E$, wherein i is a natural number and represents a median energy distribution of the ith group of photons, and an energy distribution width of the group of photons is $$\left(E_i \pm \frac{1}{2} \cdot Bin_E\right).$$

* * * * *